United States Patent
Barman

(10) Patent No.: US 9,974,593 B2
(45) Date of Patent: May 22, 2018

(54) NEUROMODULATION AND ASSOCIATED SYSTEMS AND METHODS FOR THE TREATMENT OF SEXUAL DYSFUNCTION

(71) Applicant: Medtronic Ardian Luxembourg S.a.r.l., Luxembourg (LU)

(72) Inventor: Neil Barman, Mountain View, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 738 days.

(21) Appl. No.: 14/379,902

(22) PCT Filed: Mar. 7, 2013

(86) PCT No.: PCT/US2013/029574
§ 371 (c)(1),
(2) Date: Aug. 20, 2014

(87) PCT Pub. No.: WO2013/134492
PCT Pub. Date: Sep. 12, 2013

(65) Prior Publication Data
US 2015/0088112 A1 Mar. 26, 2015

Related U.S. Application Data
(60) Provisional application No. 61/608,437, filed on Mar. 8, 2012.

(51) Int. Cl.
*A61B 18/04* (2006.01)
*A61B 18/14* (2006.01)
(Continued)

(52) U.S. Cl.
CPC ............ *A61B 18/04* (2013.01); *A61B 18/02* (2013.01); *A61B 18/1492* (2013.01);
(Continued)

(58) Field of Classification Search
CPC ......... A61B 18/02; A61B 18/04; A61B 18/14; A61B 18/1442; A61B 18/1445;
(Continued)

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

WO WO-1994007446 A1 4/1994
WO WO-1995025472 9/1995
(Continued)

OTHER PUBLICATIONS

International Search Report and Written Opinion for International App. No. PCT/US13/29574, dated May 20, 2013, 9 pages.
(Continued)

*Primary Examiner* — Michael Peffley
*Assistant Examiner* — Khadijeh Vahdat

(57) ABSTRACT

Methods for treating erectile dysfunction with therapeutic neuromodulation and associated systems and methods are disclosed herein. Erectile dysfunction can be characterized by the inability to develop and/or maintain an erection during sexual arousal or activity. One aspect of the present technology is directed to methods that at least partially inhibit sympathetic neural activity in nerves innervating the penis of a patient. Sympathetic drive in the patient can thereby be reduced in a manner that treats the patient for erectile dysfunction. Sympathetic nerve activity can be modulated along afferent and/or efferent pathways. The modulation can be achieved, for example, using an intravascularly positioned catheter carrying a therapeutic assembly, e.g., a therapeutic assembly configured to use electri-
(Continued)

cally-induced, thermally-induced, and/or chemically-induced approaches to modulate the nerves.

9 Claims, 10 Drawing Sheets

(51) Int. Cl.
  *A61B 18/00* (2006.01)
  *A61B 18/02* (2006.01)
(52) U.S. Cl.
  CPC .............. *A61B 2018/00404* (2013.01); *A61B 2018/00434* (2013.01); *A61B 2018/00577* (2013.01); *A61B 2018/00773* (2013.01); *A61B 2018/0212* (2013.01)
(58) Field of Classification Search
  CPC ............ A61B 18/1448; A61B 18/1492; A61B 2018/00404; A61B 2018/00434; A61B 2018/00577; A61B 2018/00773; A61B 2018/0212
  USPC ...................................................... 606/28–50
  See application file for complete search history.

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,093,709 A * | 7/2000 | Jirousek ............... A61K 31/407 514/183 |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,019,435 B2 | 9/2011 | Hastings et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0167509 A1 | 8/2004 | Taimisto |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2005/0240229 A1 | 10/2005 | Whitehurst et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0247266 A1 | 11/2006 | Yamada et al. |
| 2006/0271111 A1 | 11/2006 | Demarais et al. |
| 2007/0092862 A1 | 4/2007 | Gerber |
| 2007/0129720 A1 | 6/2007 | Demarais et al. |

(56) References Cited

U.S. PATENT DOCUMENTS

| | | | |
|---|---|---|---|
| 2007/0255333 A1 | 11/2007 | Giftakis et al. | |
| 2007/0265687 A1 | 11/2007 | Deem et al. | |
| 2008/0319513 A1 | 12/2008 | Pu et al. | |
| 2009/0018486 A1 | 1/2009 | Goren et al. | |
| 2009/0036948 A1 | 2/2009 | Levin et al. | |
| 2010/0069708 A1 | 3/2010 | Tajkarimi | |
| 2010/0137860 A1 | 6/2010 | Demarais et al. | |
| 2010/0137952 A1 | 6/2010 | Demarais et al. | |
| 2010/0168731 A1* | 7/2010 | Wu | A61B 18/1206 606/33 |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2011/0060324 A1 | 3/2011 | Wu et al. | |
| 2011/0172528 A1 | 7/2011 | Gertner | |
| 2011/0200171 A1* | 8/2011 | Beetel | A61N 5/1042 378/65 |
| 2011/0208175 A1 | 8/2011 | Sobotka et al. | |
| 2011/0264075 A1 | 10/2011 | Leung et al. | |
| 2012/0116382 A1 | 5/2012 | Ku et al. | |
| 2012/0130289 A1 | 5/2012 | Demarais et al. | |
| 2012/0130345 A1 | 5/2012 | Levin et al. | |
| 2012/0136350 A1 | 5/2012 | Goshgarian et al. | |
| 2012/0150267 A1 | 6/2012 | Buckley et al. | |
| 2012/0172837 A1 | 7/2012 | Demarais et al. | |

FOREIGN PATENT DOCUMENTS

| | | | |
|---|---|---|---|
| WO | WO-1995031142 A1 | 11/1995 | |
| WO | WO-1997036548 | 10/1997 | |
| WO | WO-1998042403 A1 | 10/1998 | |
| WO | WO-1999/00060 | 1/1999 | |
| WO | WO-1999000060 A1 | 1/1999 | |
| WO | WO-2001022897 | 4/2001 | |
| WO | WO-2001070114 | 9/2001 | |
| WO | WO-2003022167 | 3/2003 | |
| WO | WO-2003/082080 | 10/2003 | |
| WO | WO-2005030072 | 4/2005 | |
| WO | WO-2005041748 | 5/2005 | |
| WO | WO-2005110528 | 11/2005 | |
| WO | WO-2006041881 | 4/2006 | |
| WO | WO-2006105121 A2 | 10/2006 | |
| WO | WO-2007008954 | 1/2007 | |
| WO | WO-2007078997 A2 | 7/2007 | |
| WO | WO-2008049084 A2 | 4/2008 | |
| WO | WO-2010/067360 A2 | 6/2010 | |
| WO | WO-2013/076588 A2 | 5/2013 | |
| WO | WO-2013/134469 A1 | 9/2013 | |
| WO | WO-2013134492 | 9/2013 | |

OTHER PUBLICATIONS

European Search Report for European Application No. 13159256, dated Oct. 17, 2013, 6 pages.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul lntegr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.

(56) References Cited

OTHER PUBLICATIONS

Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol,* 174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci,* 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:11-17-11-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.

(56) References Cited

OTHER PUBLICATIONS

Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.

(56) References Cited

OTHER PUBLICATIONS

Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European U.S. Pat. No. 2465470, Granted Oct. 28, 2015, dated Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.
Stella, A., et al., "Effects of reversable renal denervation on haemodynamic and excretory functions on the ipsilateral and contralateral kidney in the cat." Hypertension, 4: 181-188 (1986).
Gong et al. "Deprival of testicular innervation induces apoptosis of Leydig cells via caspase-8-dependent signaling: A novel survival pathway revealed." Biochem Biophys Res Commun 2009; 382: 165-70.
Strom et al., "Microsurgical denervation of the spermatic cord for chronic orchialgia: long-term results from a single center." The Journal of urology 2008; 180: 949-53.
Parekattil SJ, Cohen MS. "Robotic surgery in male infertility and chronic orchialgia." Current opinion in urology 2010; 20: 75-9.
Frankel Al, Ryan El. "Testicular Innervation is Necessary for the Response of Plasma Testosterone Stress." Biology of reproduction 1981; 24: 491-5.
Pabst R, Martin O, Lippert H. Is the low fertility rate after vasovasostomy caused by nerve resection during vasectomy? Fertility and sterility 1979; 31: 316-20.
Chow, Shih-Han et al., "The Effects of Testicular Denervation on Spermatogenesis in the Sprague-Dawley Rat," Neuroendocrinology, vol. 72, 2000, 37-45.
Diedericks, W., "The Sympathetic role as an antagonist of erection," Urol Res, vol. 19, 1991, 123-126.
Kuntz, A. et al., Components and Distribution of the Spermatic Nerves and the Nerves of the Vas Deferens, St. Louis University School of Medicine, 1946, 12 pages.
Rauchenwald, M. et al., "Efferent Innervation of the Rat Testis," Biology of Reproduction, vol. 52, 1995, 1136-1143.
Brooks, J.G. et al., "Pudendal Arteriography for Erectile Dysfunction," Boston University Medical Center, Boston, MA, 2013, 1 page.
Krum et al., "Catheter-Based Renal Sympathetic Denervation for Resistant Hypertension Durability of Blood Pressure Reduction Out to 24 Months" Hypertension, 2011, vol. 57, pp. 911-917.
Schlaich et al., "Renal sympathetic nerve ablation: the new frontier in the treatment of hypertension" Current Hypertension Reports, 2010, vol. 12(1), pp. 39-46.

\* cited by examiner

*Arterial Vasculature*

*Venous Vasculature*

NEUROMODULATION AND ASSOCIATED SYSTEMS AND METHODS FOR THE TREATMENT OF SEXUAL DYSFUNCTION

CROSS-REFERENCE TO RELATED APPLICATION(S)

The present application claims priority to U.S. Provisional Patent Application No. 61/608,437, filed Mar. 8, 2012, entitled "TESTICULAR AND/OR PENILE NEUROMODULATION AND ASSOCIATED SYSTEMS AND METHODS," which is incorporated herein in its entirety by reference.

TECHNICAL FIELD

The present technology relates generally to neuromodulation and associated systems and methods for the treatment of sexual dysfunction. In particular, the present technology relates to sympathetic nerve neuromodulation for the treatment of erectile dysfunction.

BACKGROUND

Sexual dysfunction disorders or problems can occur in adult men of any age, but may be more common in aging men or men with other health-related conditions. The most common sexual dysfunction disorders in men include erectile dysfunction (e.g., impotence), ejaculation disorders (e.g., premature ejaculation, inhibited ejaculation, retrograde ejaculation) and inhibited sexual desire (e.g., reduced libido). Erectile dysfunction (ED) is a sexual dysfunction disorder affecting the ability to develop or maintain an erection of the penis during sexual performance or activity and can be associated with certain diseases and conditions such as diabetes, cardiovascular disorders (e.g., atherosclerosis, hypertension), nerve damage, injury to the penis, etc. Other male sexual dysfunction problems, such as inhibited sexual desire or low libido can be associated with low levels of the hormone testosterone as well as other medical diseases or conditions, including diabetes and hypertension.

The prevalence of sexual dysfunction in men is estimated as being high (e.g., about 30% of adult men). For example, ED affects as many as 30 million men in the United States, including up to 30 to 50 percent of men between the ages of 40 and 70. Many factors and diseases (e.g., hypertension, diabetes, kidney disease) can cause or contribute to the various forms of sexual dysfunction and diagnostic testing, such as blood tests (e.g., for hormone levels), vascular assessment (e.g., evaluation of blood flow to the penis), sensory testing (e.g., measurements of the strength of nerve impulses) and nocturnal penile tumescence and rigidity testing (e.g., to rule out psychological causes of ED) are performed to assess the likely treatment protocols to be administered to address the sexual dysfunction. Treatments often only address specific sequelae (e.g., individual symptoms or indications) of the sexual dysfunction as opposed to an underlying condition or disease; however, such treatments may be combined with other medications (e.g., antihypertensive therapy, diabetic/insulin-regulating therapies, etc.) administered for health-related conditions either causing, contributing, or associated with the sexual dysfunction. Accordingly, many patients can be required to combine multiple treatment programs for treating these conditions and/or complications separately. For example, men diagnosed with ED can be prescribed medications that increase blood flow to the penis (e.g., sildenafil, tadalafil, vardenafil, avanafil, etc.), supplemental hormone therapy (e.g., testosterone replacement therapy), and medical devices (e.g., vacuum devices, penile implants, etc.). Such pharmacologic and/or medical device use strategies, however, have significant limitations including limited efficacy, side effects, long-term maintenance regimens, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology is directed to apparatuses, systems, and methods for treating sexual dysfunction and/or improving one or more measurable physiological parameters corresponding to sexual dysfunction, such as ED, using penile and/or renal neuromodulation. For example, some embodiments include performing therapeutically-effective penile and/or renal neuromodulation on a patient diagnosed with ED. In other examples, several embodiments are directed to modulation of sympathetic penile nerves to treat ED and related sexual dysfunction conditions, such as low libido. Further embodiments are directed to modulation of renal sympathetic nerves to reduce central sympathetic activity for the treatment of sexual dysfunction, such as ED. As discussed in greater detail below, penile and/or renal neuromodulation can include rendering neural fibers inert, inactive, or otherwise completely or partially reduced in function. This result can be electrically-induced, thermally-induced, or induced by another mechanism during a neuromodulation procedure, e.g., a procedure including percutaneous transluminal intravascular access.

Specific details of several embodiments of the technology are described below with reference to FIGS. 1-10B. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-10B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. SEXUAL DYSFUNCTION AND PHYSIOLOGY

A. Penile Anatomy and Physiology

Figure 1:
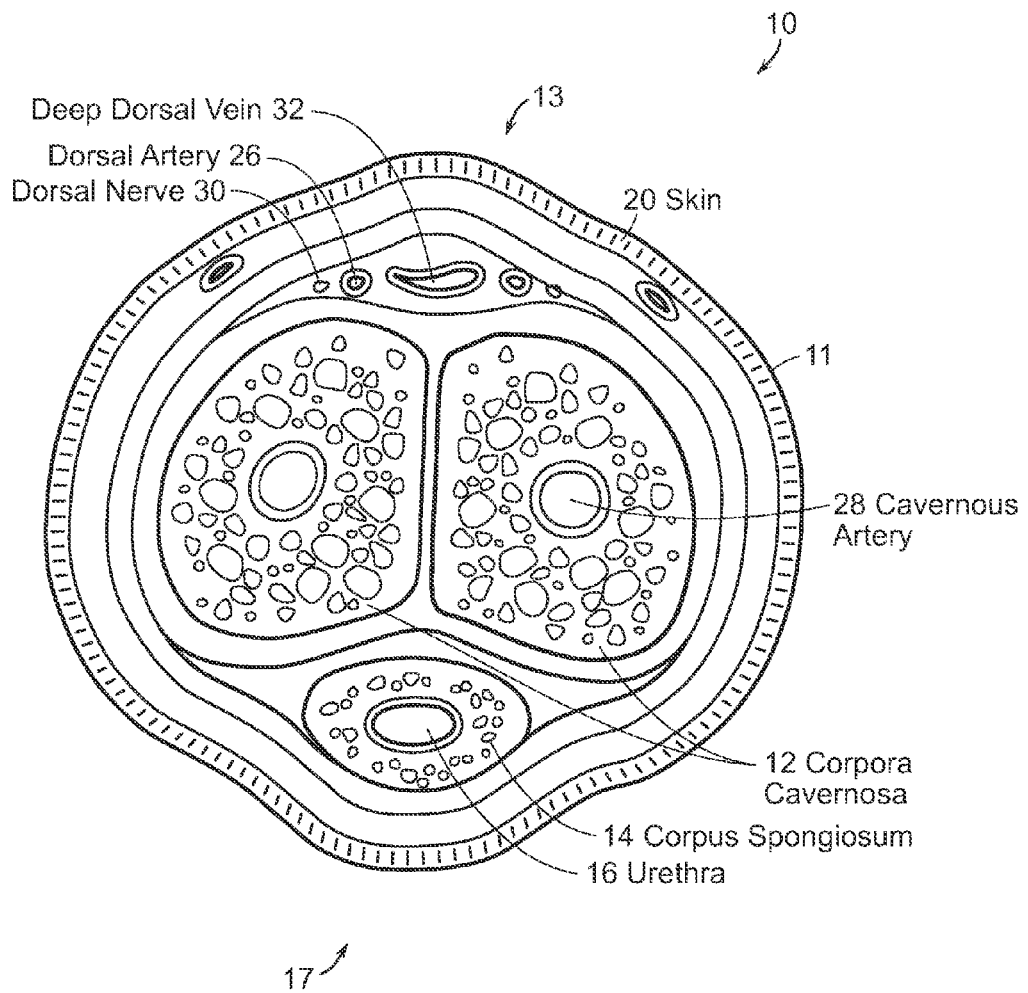
FIG. 1 is a cross-sectional view of the shaft of the penis showing penile structures, vessels and nerves.

The penis is part of the external genitalia of male humans that serves as both a reproductive organ and as urinary duct. The penis is made up of the root or radix (e.g., which lies within the superficial perineal pouch), the body or corpus which includes dorsal and ventral/urethral facing surfaces, and an epithelium consisting of the shaft skin, the foreskin, the preputial mucosa and the glans penis at the distal end of the organ. FIG. 1, for example, is a cross-sectional view of the shaft of the penis 10 showing penile structures, vessels and nerves. The penile shaft 11 comprises three columns of erectile tissue surrounded by the columns' fascial layers, nerves, lymphatic and blood vessels. The corpora cavernosa 12 are paired columns of erectile tissue on the dorsal side 13 of the shaft 11 and the corpus spongiosum 14 which surrounds the urethra 16 is aligned along the ventral side 17 of the shaft 11. The erectile tissue within the corpora contains arteries, nerves, muscle fibers, and venous sinuses lined with flat endothelial cells.

Figure 2:
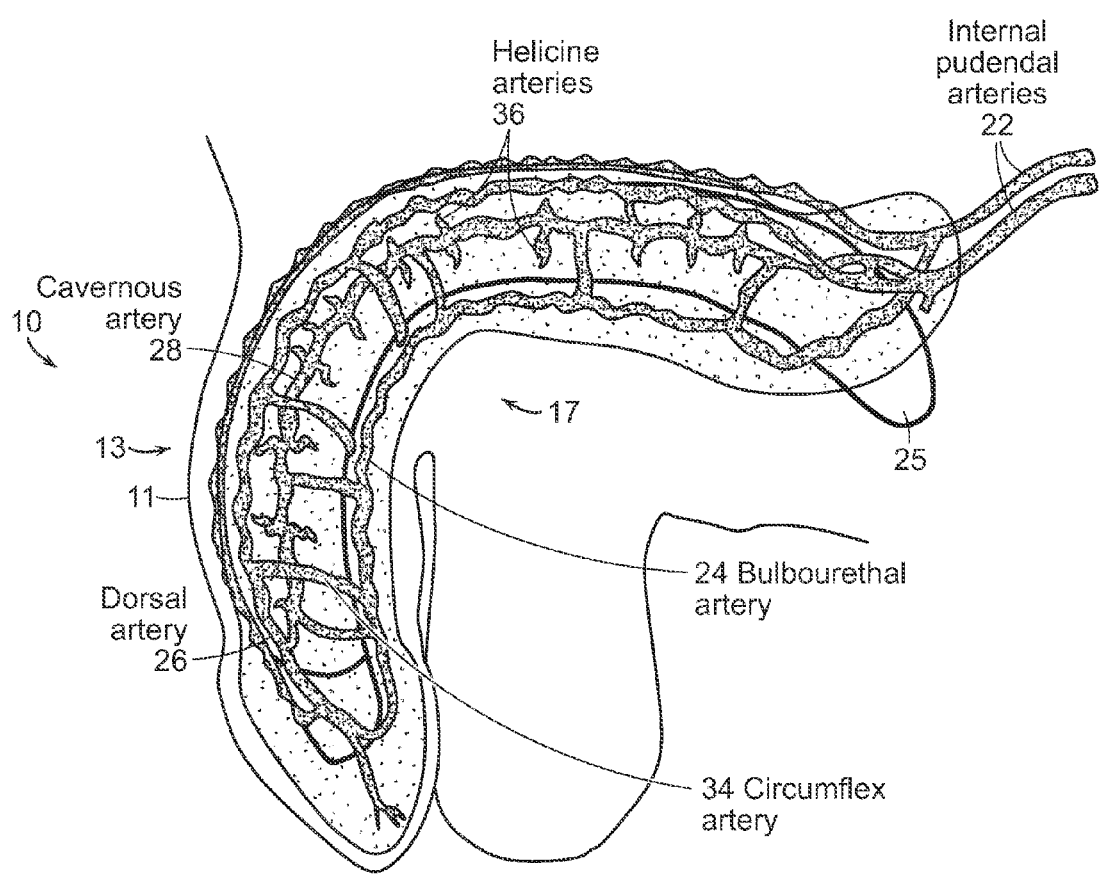
FIG. 2 is an anatomical view illustrating the arterial vasculature of the human penis.

FIG. 2 is an anatomical view illustrating the arterial vasculature of the human penis. Referring to FIGS. 1 and 2 together, the blood supply to deep structures of the penis 10 is derived from a continuation of the left and right internal pudendal arteries 22, while blood supply to the skin 20 of the penis 10 is from the left and right superficial external pudendal arteries (not shown), which arise from the femoral arteries (not shown). Three main arterial branches that flow to the penis 10 from the internal pudendal artery 22 are the bulbourethral artery 24, the dorsal artery 26, and the cavernosa artery 28. The bulbourethral artery 24 passes through the deep penile fascia to enter and supply the bulb of the penis 25 and penile urethra 16. The dorsal artery 26 travels along the dorsal side 13 of the penis 10 between the dorsal nerve 30 and deep dorsal vein 32 and gives off circumflex arterial branches 34 that accompany the circumflex veins (not shown). The blood flow to the corpora cavernosa 12 is via deep arteries of the penis (the cavernosal arteries 28), which run near the center of each corpus cavernosum 12. The cavernosal artery 28 is usually a single artery that arises on each side and enters the corpus cavernosum 12 at the crus and runs the length of the penile shaft 11, giving off the helicine arteries 36, which are an integral component of the erectile process.

Figure 3:
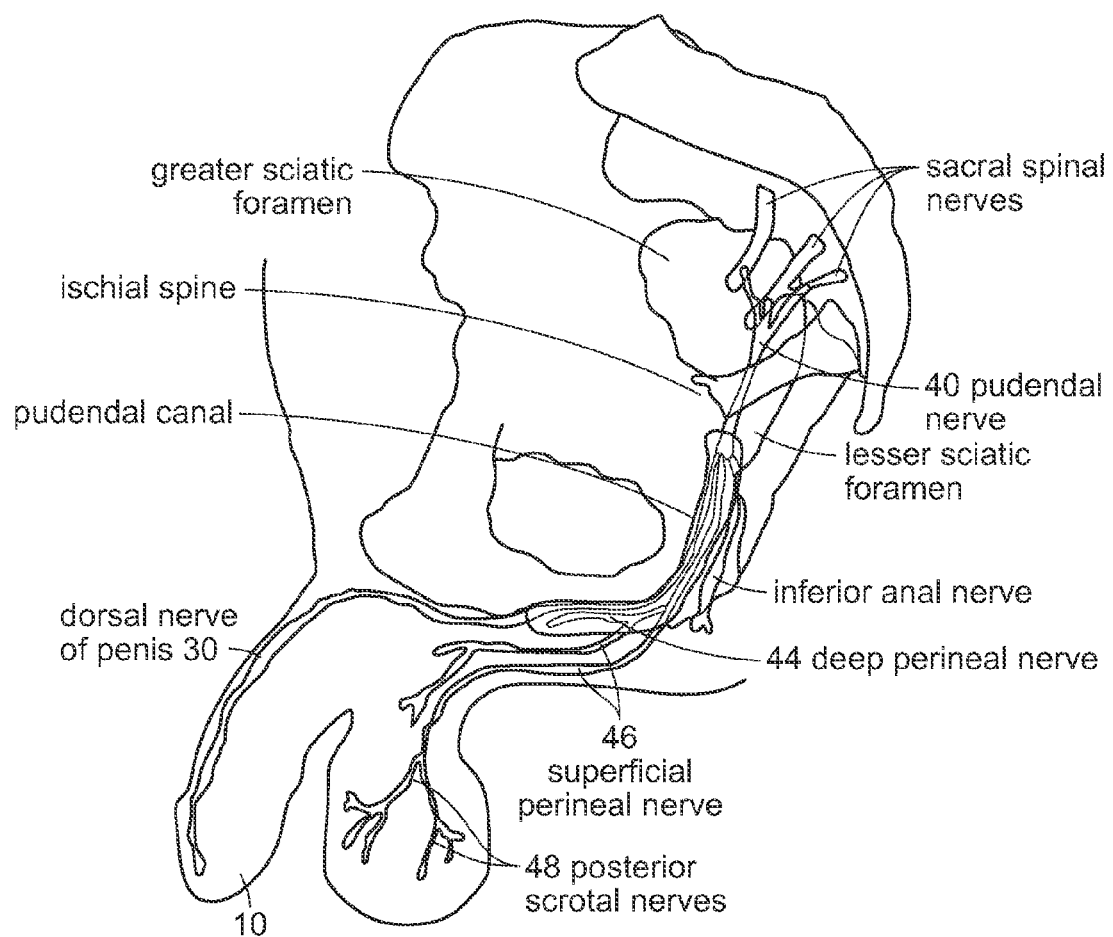
FIG. 3 is an anatomical view illustrating nerves innervating penile and scrotal tissue.

FIG. 3 is an anatomical view illustrating nerves innervating penile and scrotal tissue. Referring to FIGS. 1-3 together, the nerves to the penis 10 are derived from the pudendal 40 and cavernous nerves (not shown). The pudendal nerves 40 supply sympathetic (e.g., somatic motor and sensory) innervation to the penis 10. For example, the post-synaptic sympathetic fibers arising from the pudendal nerve 40 innervate penile erectile tissue (e.g., corpora cavernosa 12, corpus spongiosum 14) to induce tonic coiling of the helicine arteries 36 of the penis 10. The helicine arteries 36 have an intimal cushion (e.g., smooth muscle that occludes the lumen of the arteries) and valves to functionally control blood flow to the erectile tissue. Sympathetic nerve stimulation maintains the tonic contractile state of the intimal cushion, thereby blocking blood flow through the occluded helicine arteries 36. Accordingly, under sympathetic nerve control, the helicine arteries 36 remain closed and blood flow is routed to arteriovenous anastomoses, through which blood normally bypasses the erectile tissue of corpora cavernosa 12, for example, and leaves the penile tissue through the deep dorsal vein 32 (FIG. 1).

The cavernous nerves (not shown) run in the crus and corpora of the penis 10, primarily dorsomedial to the cavernous arteries 28 and are a combination of parasympathetic and visceral afferent fibers that provide nerve supply to the erectile tissue. During sexual arousal, parasympathetic stimulation (e.g., from the cavernous nerves), removes the tonic state and allows vasodilation of the intimal cushion of the helicine arteries 36. Accordingly, upon parasympathetic stimulation, blood can now flow through the helicine arteries 36 and through capillaries to pool in the corpora cavernosa 12, resulting in erection (e.g., tumescence of the penile erectile tissue). The valves present in the helicine arteries 36 prevent backflow from the corpora cavernosa 12 which are now engorged and under greater pressure. The parasympathetic relaxation response is mediated by the release of nitric oxide (NO) from nonadrenergic, noncholinergic neurons. The NO binds receptors of the enzyme guanylate cyclase, thereby increasing levels of cyclic guanosine monophosphate (cGMP), which relaxes cavernosal smooth muscle.

Accordingly, sympathetic drive maintains the helicine arteries 36 in a contracted and tortuous state, thereby maintaining a flaccid penile state, while parasympathetic drive dilates and straightens the helicine arteries 36, thereby allowing the penis 10 to transform to an erect state. Intracavernous pressure increases and is further increased by contraction of ischiocavemous and bulbospongiosus muscles (not shown), compressing venous outflow, thereby resulting in full rigidity.

B. Erectile Dysfunction

ED is defined as the inability to achieve and maintain an erection sufficient to allow for satisfactory sexual intercourse. ED significantly impacts the quality of life of a patient suffering from this sexual dysfunction and the incidence of ED will likely increase as the life-span of men increase and/or as male patients develop more risk factors (e.g., hypertension, kidney disease, prostate diseases, diabetes, etc.). Multiple etiological factors may be responsible for or can vary the severity of ED including vascular, neurological, endocrine, and psychological factors. Common risk factors can include, for example, hypertension, smoking, diabetes, pelvic irradiation, pelvic or penile injury, among others. For example, certain medications, such as anti-anxiety/anti-depression or anti-hypertensive pharmaceutical medications can also impact erectile functionality.

A patient suspected of having ED can be assessed using various diagnostic testing methods to determine the cause and/or determine a proposed treatment regimen. For example, blood tests can be used to assess hormone levels (e.g., testosterone, luteinizing hormone, prolactin, and/or thyroid hormone). Vascular assessment, such as by magnetic resonance angiography, can evaluate viability of the arterial and venous systems controlling blood flow to the penis. Additional vascular testing can include penile prostaglandin injection followed by duplex ultrasound to detect vascular dilation and measure penile blood pressure for evaluation of blood flow, venous leak, signs of atherosclerosis or other problems associated with erectile tissue. Sensory testing, such as the bulbocavernosus reflex test can provide measurements of the strength of nerve impulses to the penis (e.g., for assessing nerve damage). Other sensory testing can include penile biothesiometry (e.g., electromagnetic vibration) to evaluate sensitivity and nerve function in the glans and shaft of the penis. Nocturnal penile tumescence and rigidity testing that monitor reactions that occur naturally during sleep (e.g., via electronic monitoring devices) can assist in differentiating between psychosomatic and physiological causes of ED. Vascular pressure in the corpora cavernosa (e.g., the erectile tissue of the penis) can be assessed during an erection using dynamic infusion cavernosometry (e.g., pumping of fluid into the penis at a known rate and pressure) or by corpus cavernosometry in which saline is infused under pressure into the corpus cavernosum and the flow rate needed to maintain an erection indicates the degree of venous leakage.

Some experimental data and clinical results are suggestive of the role the sympathetic nervous system has as a contributor to ED. For example, detumescence (e.g., diminution of erection) by sympathetic trunk stimulation was determined experimentally in canine studies (Diederichs et al., 1990, Urology Research 19: 123-126; incorporated herein by reference in its entirety). Moreover, these studies also demonstrated that stimulation of the sympathetic trunk prevented erection entirely, despite simultaneous stimulation of the parasympathetic nerves (e.g., the cavernous nerves) of the penis, which naturally increases blood flow to the penile erectile tissue for developing and maintaining erection. Additionally, the degree of sympathoexcitation may be related to the degree of ED severity. Without being bound by theory, these results may suggest that a parasympathetic threshold level of stimulation must be achieved to overcome a sympathetic level of stimulation to the penile erectile tissue. For example, if the level of sympathoexcitation is higher than normal for a patient having ED, the parasympathetic threshold level of stimulation necessary to achieve an erection, is higher than normal.

Further evidence suggests that hypertension and ED are related conditions. For example, disturbance of endothelium-derived factors (e.g., endothelium-derived hyperpolarizing factor, endothelium-derived relaxing factor, NO) can lead to an increase in vascular smooth muscle (VSM) contraction, which systemically can cause hypertension, and locally (e.g., in the penis) can prevent dilation of the arteries (e.g., the coiled helicine arteries 36) supplying the corpora cavernosa and corpus spongiosum, thereby preventing erection. Accordingly, and in further embodiments, male patients with self-reported or clinically diagnosed physiological ED can be assessed for elevated sympathetic nerve activity (e.g., overactivity or hyperactivity), including establishing measurements for markers of elevated sympathetic nerve activity, e.g., muscle sympathetic nerve activity (MSNA), penile or total body plasma norepinephrine spillover levels, and heart rate variability. Additional diagnosis can be performed for male patients reporting ED, for example, to assess a patient's heart condition (e.g., blood pressure testing), metabolic condition (e.g., insulin sensitivity) or for markers of renal injury e.g., serum blood urea nitrogen (BUN) levels, serum creatinine levels, serum cystatin C levels, proteinuria levels, neutrophil gelatinase-associated lipocalin (NGAL) levels, and kidney injury molecule-1 (Kim-1) levels).

II. NEUROMODULATION FOR TREATMENT OF SEXUAL DYSFUNCTION

The sympathetic nervous system (SNS) is a primarily involuntary bodily control system typically associated with stress responses. Fibers (e.g., efferent and/or afferent neural fibers) of the SNS extend through tissue in almost every organ system of the human body. For example, and as described above, SNS fibers innervate the male reproductive organs, including the erectile tissue of the penis. While sympathetic drive regulation can have adaptive utility in maintaining homeostasis or in preparing many organs in the body for a rapid response to environmental factors, chronic activation of the SNS can drive the progression of many disease states as well as sexual dysfunction problems such as ED.

A. Sympathetic Penile Nerves

Testicular and/or penile sympathetic nerves (e.g., sympathetic nerves along the testicular vessels, pudendal vessels or other associated structures), innervate portions of the male genitalia. As discussed above and with respect to FIGS. 1-3, the pudendal nerve 40, which is derived from the sacral plexus (e.g., sacral spinal nerves 42, FIG. 3), accompanies the internal pudendal vessels (e.g., internal pudendal artery) to innervate male genitalia, such as the penis 10 and the scrotum. For example, the pudendal nerve 40 eventually gives rise to the deep perineal nerve 44, the superficial perineal nerve 46 and the dorsal nerve 30 of the penis 10 in males. The superficial perineal nerve 46, which sits adjacent and below the internal pudendal artery 22, becomes the posterior scrotal nerves 48 in males. The dorsal nerve 30 of the penis 10 accompanies the internal pudendal artery 22, which is a branch of the internal iliac artery, and the dorsal artery 26 of the penis 10. Additional sympathetic nerves to the penis descend through the inferior mesenteric plexus and the inferior hypogastric plexus, which accompany the branches of the internal iliac artery (not shown). Stimulation of sympathetic nerves innervating the penis, such as the hypogastric nerve or the sympathetic trunk causes no change in intracavernosal pressure, but stimulation during an established erection causes penile detumescence. To treat ED or reduce a severity of ED (e.g., reduce frequency of impotence), at least partial neuromodulation of these nerve fibers can be performed.

B. Sympathetic Renal Nerves

Figure 4:
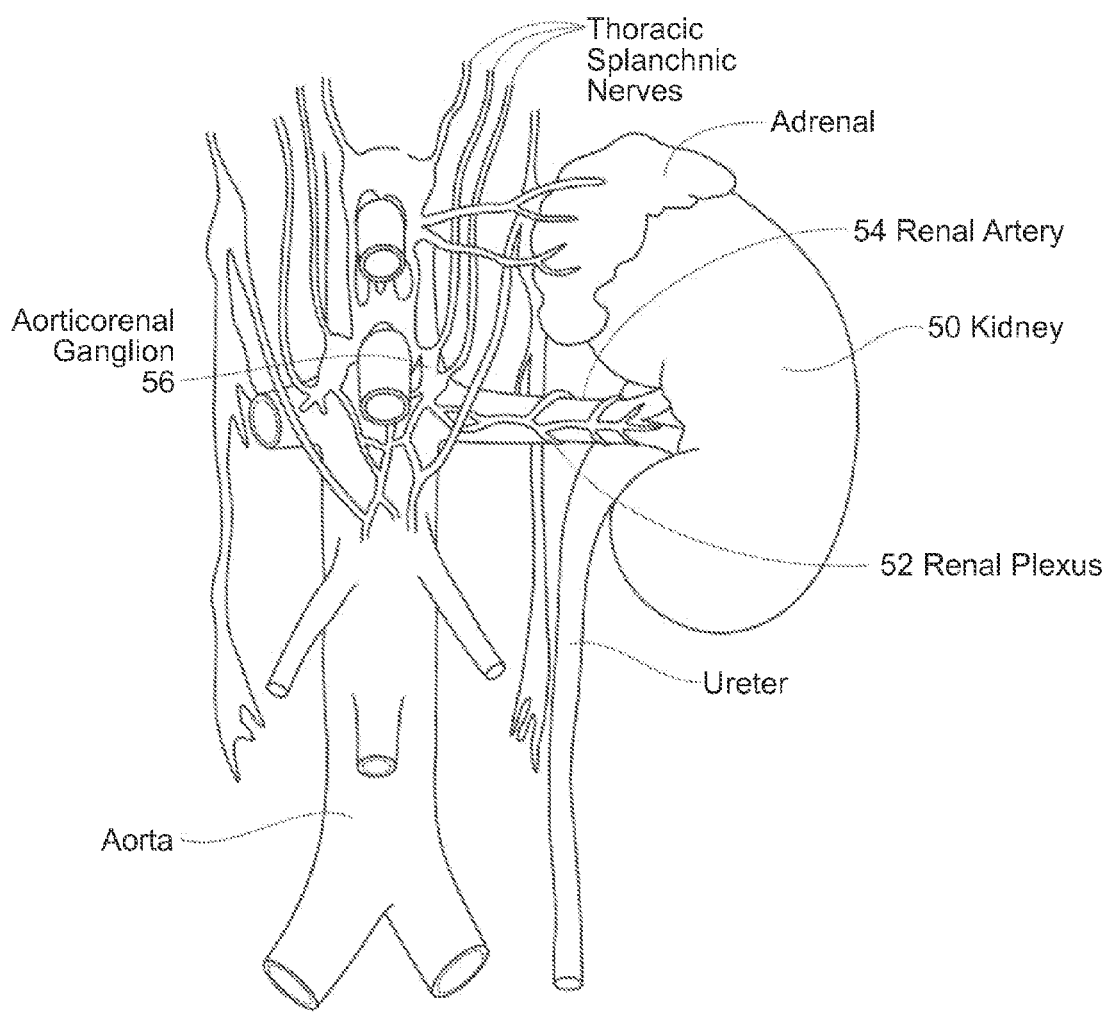
FIG. 4 is an enlarged anatomic view of nerves of a left kidney to form the renal plexus surrounding the left renal artery.

As FIG. 4 shows, the kidney 50 is innervated by the renal plexus 52, which is intimately associated with the renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50. Fibers contributing to the renal plexus 52 arise from the celiac ganglion (not shown), the superior mesenteric ganglion (not shown), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion, the superior mesenteric ganglion, and the aorticorenal ganglion 56. Postganglionic neuronal cell bodies exit the celiac ganglion, the superior mesenteric ganglion, and the aorticorenal ganglion 56 to the renal plexus 52 and are distributed to the renal vasculature.

As provided herein, renal neuromodulation is expected to be useful in the treatment of ED. Further, such therapy is expected to be particularly useful in the treatment of ED in patients also having one or more clinical conditions characterized by increased central sympathetic activity (e.g., hypertension, metabolic syndrome, insulin resistance, diabetes, etc.). Without being bound by theory, it is believed that since the reduction of afferent neural signals contributes to the systemic reduction of sympathetic tone/drive, renal neuromodulation may be useful in treating ED. For example, a reduction in central sympathetic drive may reduce the incidence of erectile dysfunction and/or eliminate sexual dysfunction issues in a male patient.

C. Neuromodulation of Sympathetic Penile and/or Renal Nerves

Sympathetic penile neuromodulation is the partial or complete incapacitation or other effective disruption or regulation of sympathetic nerves innervating the penis, e.g., nerves terminating in or originating from the penis or in structures closely associated with a penis. In another embodiment, renal neuromodulation is the partial or complete incapacitation or other effective disruption of nerves innervating the kidneys. In particular, penile neuromodulation or renal neuromodulation comprises inhibiting, reducing, blocking, pacing, upregulating, and/or downregulating neural communication along sympathetic neural fibers (e.g., efferent and/or afferent neural fibers) innervating the penis (e.g., penile erectile tissue) or kidney, respectively. Such incapacitation, disruption, and/or regulation can be long-term (e.g., permanent or for periods of months, years, or decades) or short-term (e.g., for periods of minutes, hours, days, or weeks). In a particular example, while long-term disruption of the penile sympathetic nerves may be desirable for alleviating symptoms associated with ED over longer periods of time, short-term modulation of the penile sympathetic nerves may also be desirable. For example, some patients may benefit from short-term modulation to address temporary sexual dysfunction issues following surgery (e.g., pelvic surgery, prostate surgery, etc.) or while prescribed a short-term pharmaceutical regimen (e.g., cancer therapy).

In one embodiment, selectively targeting efferent sympathetic penile nerves (e.g., by the purposeful application of energy and/or chemicals) may result in a beneficial treatment of ED and other related sexual disorders in men. By way of theory, selective modulation of efferent nerve fibers innervating the penile tissue, and particularly the penile erectile tissue, over afferent nerve fibers and/or parasympathetic nerve fibers, can, in some embodiments, treat the patient for ED. For example, at least partial preservation of afferent nerve fibers can be beneficial for transmitting pleasure signals (e.g., during sexual activity) to the brain. Additionally, and as described previously, parasympathetic stimulation (e.g., during sexual arousal or performance) causes erection of the penile tissue. In one embodiment, a reduction in efferent sympathetic drive to penile tissue may reduce a level of inhibition of erection such that parasympathetic nerve stimulation can meet or exceed a parasympathetic threshold level for developing and/or maintaining an erection during sexual activity or performance. Selective neuromodulation can include modulating efferent sympathetic nerves preferentially over afferent sympathetic nerves or, in another embodiment, modulating efferent sympathetic nerves preferentially over parasympathetic nerves. Complete selectivity may not be necessary, but rather several embodiments include modulating the efferent sympathetic nerves to a greater extent than the afferent sympathetic and/or parasympathetic nerves. Such selectivity could be made for example, by selecting a treatment location where the number of efferent nerve fibers is higher than the number of afferent nerve fibers and/or parasympathetic nerve fibers. In other embodiments, selectively could be made via chemicals or drugs that have selective protective or damaging properties to, for example, the presence or absence of myelination, or in another embodiment, to a receptor (e.g., norepinephrine receptor, acetylcholine receptor).

Further embodiments can include partial neuromodulation to bring the number of functioning renal sympathetic nerves in a patient diagnosed with ED down to at or near normal levels, or in another embodiment, down to a level below normal. In some instances, partial neuromodulation may be effective in treating ED. As such, disclosed herein are methods and devices for achieving partial neuromodulation at or near the target blood vessel, as well as methods of treating ED using these partial neuromodulation techniques. Accordingly, in some embodiments, neuromodulation may be carried out in a non-selective manner. In these embodiments, treatment results in modulation (e.g., ablation) of a random subset of the total nerves in the region being targeted. For example, while non-selective partial neuromodulation can modulate or ablate a portion of afferent penile sympathetic nerves, the patient may retain enough nerve functionality to preserve the benefits of penile sensitivity and/or be able to transmit pleasure signals while still treating ED. In other embodiments, partial neuromodulation may be carried out in a selective manner. In these embodiments, treatment results in modulation (e.g., ablation) of a specific subset of the total nerves in the region being targeted. For example, in certain embodiments renal neuromodulation may specifically target penile efferent sympathetic nerves. Embodiments that specifically target efferent or afferent sympathetic nerves may do so by focusing on tissue regions that contain a particularly high concentration of the target nerves.

Central sympathetic neural overactivity can cause or exacerbate several sexual dysfunction conditions, including, but not limited to, ED, dysfunctional hormone or steroid production, and/or low libido. Renal neuromodulation, e.g., for reducing central sympathetic activity level, is also expected to be useful in treating these conditions. Methods and systems for sympathetic penile neuromodulation or renal neuromodulation for efficaciously treating several clinical conditions characterized by increased penile sympathetic activity, such as ED and associated conditions, are described herein.

Furthermore, penile sympathetic activity may contribute to central sympathetic tone or drive. Accordingly, sympathetic penile neuromodulation may be useful in treating clinical conditions associated with central sympathetic activity (e.g., overactivity or hyperactivity), particularly conditions associated with central sympathetic overstimulation. As mentioned previously, conditions associated with central sympathetic activity (e.g., overactivity or hyperactivity) include, for example, hypertension, heart failure, acute myocardial infarction, metabolic syndrome, insulin resistance, diabetes, left ventricular hypertrophy, chronic and end-stage renal disease, inappropriate fluid retention in heart failure, cardio-renal syndrome, polycystic kidney disease, osteoporosis, and sudden death, among other conditions.

By way of theory, targeting sympathetic penile nerves (e.g., via a catheter-based approach, extracorporeal ultrasound, etc.) may cause beneficial effects extending well beyond the penis and other male genital organs, such as reducing cardiovascular risk. The role of sympathetic activation for blood pressure regulation is well established, as is the relevance of increased renal sympathetic nerve activity for alterations in renal blood flow and glomerular filtration rate. There is now also clear evidence that sympathetic activation results in adverse consequences on metabolic control, including insulin sensitivity. Additionally, overactivity of the sympathetic nervous system is implicated in the specific etiology of ED. Some aspects of methods of treating patients having ED using sympathetic penile neuromodulation are at least in part derived from the recognition described herein that the male reproductive organs (e.g., penis, scrotum, testes) may contribute to elevated central sympathetic drive.

Several properties of the penile vasculature may inform the design of treatment devices and associated methods for achieving sympathetic penile neuromodulation, for example, via intravascular access, and impose specific design requirements for such devices. Specific design requirements may include percutaneously accessing the vasculature (e.g., internal pudendal vessels, the dorsal artery of the penis and/or the internal iliac vessels), facilitating stable contact between the energy delivery elements of such devices and a luminal surface or wall of the vasculature, and/or effectively modulating the sympathetic penile nerves with the neuromodulatory apparatus.

Intravascular devices that reduce sympathetic nerve activity by applying, for example, radio frequency (RF) energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. Renal neuromodulation is expected to reduce renal sympathetic neural activity, causing a reduction in renin production, and decreased aldosterone production. Additionally, since the reduction of afferent neural signals contributes to the systemic reduction of sympathetic tone/drive, renal denervation might be useful in treating multiple conditions associated with systemic sympathetic hyperactivity.

Accordingly, renal neuromodulation is expected to be useful in treating ED. The beneficial effect of renal neuromodulation with respect to ED is expected to apply regardless of the baseline renal sympathetic neural activity. For example, renal neuromodulation in accordance with embodiments of the present technology can improve one or more measurable physiological parameters corresponding to ED when baseline renal sympathetic neural activity is normal, below normal, or above normal (e.g., hyperactive or overactive). In addition to the effect on central sympathetic drive, by reducing blood pressure, renal denervation may lead to reduced need for anti-hypertensive medications, many of which have been shown to cause ED as a side-effect. In another embodiment, by reducing central sympathetic drive, renal neuromodulation can lower a parasympathetic threshold for stimulating an erection and/or maintaining an erection, even if baseline renal sympathetic or central sympathetic neural activity is about normal or below normal.

As described above with respect to the design of treatment devices and associated methods for penile sympathetic neuromodulation, several properties of the renal vasculature may inform the design of treatment devices and associated methods for achieving renal neuromodulation, for example, via intravascular access, and impose specific design requirements for such devices. Specific design requirements for renal neuromodulation may include accessing the renal artery, a renal vein, a ureter, a renal pelvis, a major renal calyx, a minor renal calyx, and/or another suitable structure, facilitating stable contact between the energy delivery elements of such devices and a luminal surface or wall of the suitable targeted structure, and/or effectively modulating the renal nerves with the neuromodulatory apparatus.

III. SELECTED EXAMPLES OF NEUROMODULATION MODALITIES

Various techniques can be used to partially or completely incapacitate neural pathways, such as those innervating the penis and/or the kidneys. As noted above, sympathetic nerve neuromodulation in accordance with embodiments of the present technology can be electrically-induced, thermally-induced, chemically-induced, or induced in another suitable manner or combination of manners at one or more suitable treatment locations during a treatment procedure. For example, the purposeful application of RF energy (monopolar and/or bipolar), pulsed RF energy, microwave energy, optical energy, ultrasound energy (e.g., intravascularly delivered ultrasound, extracorporeal ultrasound, high-intensity focused ultrasound (HIFU)), cryotherapeutic energy, direct heat energy, chemicals (e.g., drugs or other agents), or combinations thereof to tissue at a treatment location can induce one or more desired effects at the treatment location, e.g., broadly across the treatment location or at localized regions of the treatment location.

Referring back to FIGS. 1-3 together and in one embodiment, treatment procedures for penile sympathetic neuromodulation can include applying a treatment modality at one or more treatment locations proximate a structure having a relatively high concentration of sympathetic nerves innervating the penis. In some embodiments, for example, at least one treatment location can be proximate a portion of the internal pudendal artery 22 or internal pudendal vein, a branch of the internal pudendal artery 22 or a branch of the internal pudendal vein, the dorsal artery 12 of the penis 10, the dorsal vein 32 of the penis 10, an ostium of the dorsal artery 12, and/or another suitable structure (e.g., other branches of the internal iliac artery) in the vicinity of penile sympathetic nerves.

Figure 5:
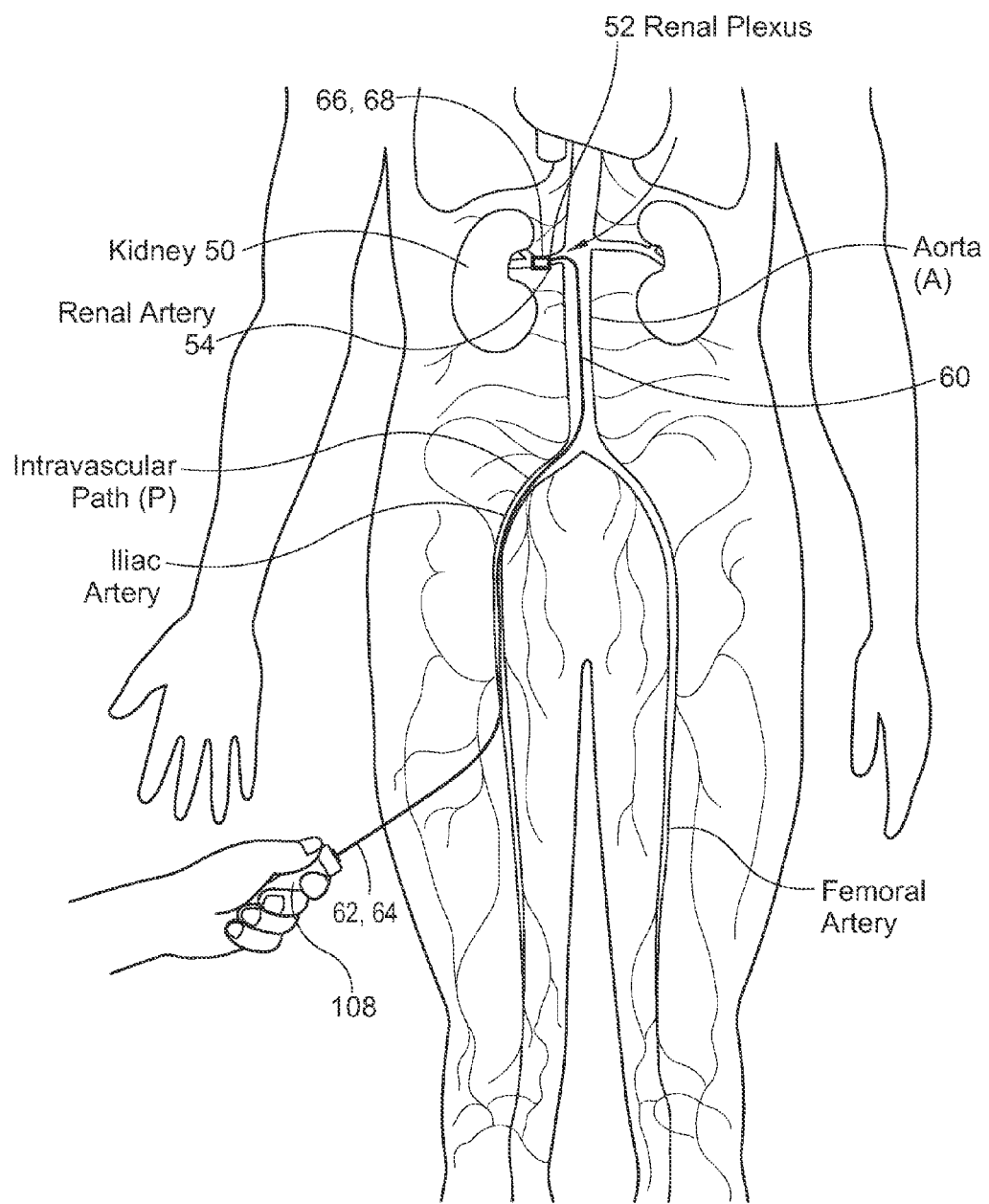
FIG. 5 illustrates modulating renal nerves with a neuromodulation system configured in accordance with an embodiment of the present technology.

Referring back to FIG. 4 and in another embodiment, treatment procedures for renal neuromodulation can include applying a treatment modality at one or more treatment locations proximate a structure having a relatively high concentration of sympathetic nerves innervating the kidneys. For example, at least one treatment location can be proximate a portion of the renal artery 54, an ostium of the renal artery 54, a renal vein (not shown), and/or another suitable structure. For example, in one embodiment, the treatment location can be a ureter, a renal pelvis, a major renal calyx, a minor renal calyx, and/or another suitable structure for selective afferent renal modulation. Examples of suitable systems, devices and methods for selective afferent renal modulation are described in co-pending International Patent Application No. PCT/US13/29526, filed Mar. 7, 2013, and incorporated herein by reference in its entirety. The disclosures of both of these applications are hereby incorporated by reference herein in their entirety. FIG. 5, for example, is a cross-sectional view illustrating neuromodulation at a treatment location within the renal artery 54. As shown in FIG. 5, a treatment device 60 including a shaft 62 and a therapeutic element 68 can be extended toward the renal artery 54 to locate the therapeutic element 68 at the treatment location within the renal artery 54. The therapeutic element 68 can be configured for neuromodulation at the treatment location via a suitable treatment modality, e.g., cryotherapeutic, direct heat, electrode-based, transducer-based, chemical-based, or another suitable treatment modality.

The treatment location can be proximate (e.g., at or near) a vessel or chamber wall (e.g. internal pudendal artery 22 or internal pudendal vein, a branch of the internal pudendal artery 22 or branch of the internal pudendal vein, the dorsal artery 12 of the penis 10, the dorsal vein 32 of the penis 10, an ostium of the dorsal artery 12, renal artery 54, an ostium of the renal artery 54, a renal vein (not shown), and/or another suitable structure for the treatment of ED), and the treated tissue can include tissue proximate the treatment location. For example, with regard to the internal pudendal artery 22, a treatment procedure can include modulating the pudendal nerve 40, which lay at least partially within or adjacent to the adventitia of the internal pudendal artery 22. In some embodiments it may be desirable to modulate penile sympathetic nerves from a treatment location within a vessel and in close proximity to or within the penis, e.g., closer to the penis erectile tissue than to a trunk of the vessel. This can increase the likelihood of modulating nerves specific to the erectile tissue, while decreasing the likelihood of modulating nerves that extend to other organs. Vessels can decrease in diameter and become more tortuous as they extend toward the penis. Accordingly, modulating penile sympathetic nerves from a treatment location in close proximity to the penis can include using a device (e.g., a treatment device similar to the treatment device 60, FIG. 5) having size, flexibility, torque-ability, kink resistance, and/or other characteristics suitable for accessing narrow and/or tortuous portions of vessels.

In some embodiments, the purposeful application of energy (e.g., electrical energy, thermal energy, etc.) to tissue can induce one or more desired thermal heating and/or cooling effects on localized regions of the target vessels, for example, and adjacent regions along all or a portion of the targeted sympathetic nerve fibers, which lay intimately within or adjacent to the adventitia of the target vessels. Some embodiments of the present technology, for example, include cryotherapeutic neuromodulation, which can include cooling tissue at a target site in a manner that modulates neural function. The mechanisms of cryotherapeutic tissue damage include, for example, direct cell injury (e.g., necrosis), vascular injury (e.g., starving the cell from nutrients by damaging supplying blood vessels), and sub-lethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Several embodiments of the present technology include cooling a structure at or near an inner surface of a vessel or chamber wall such that proximate (e.g., adjacent) tissue is effectively cooled to a depth where sympathetic (efferent and/or afferent) nerves reside. For example, a cooling structure can be cooled to the extent that it causes therapeutically-effective, cryogenic nerve modulation. Sufficiently cooling at least a portion of a penile sympathetic nerve may reduce the sympathetic drive to the penile erectile tissue in a manner that can reduce a parasympathetic threshold for stimulating an erection and/or maintaining an erection. In some embodiments, a cryotherapeutic treatment modality can include cooling that is not configured to cause neuromodulation. For example, the cooling can be at or above cryogenic temperatures and can be used to control neuromodulation via another treatment modality, e.g., to reduce damage to non-targeted tissue when targeted tissue adjacent to the non-targeted tissue is heated.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the internal and/or external organ structures to rise and fall and thereby move the associated vasculature. In addition, blood flow is pulsatile and can cause structures associated with the target organs (e.g., penis, kidneys) to pulse. Cryogenic adhesion also can facilitate intravascular positioning, particularly in relatively small structures (e.g., relatively short arteries) in which stable intravascular positioning can be difficult to achieve.

As an alternative to or in conjunction with cryotherapeutic cooling, other suitable energy delivery techniques, such as electrode-based or transducer-based approaches, can be used for therapeutically-effective neuromodulation. Electrode-based or transducer-based treatment can include delivering electrical energy and/or another form of energy to tissue and/or heating tissue at a treatment location in a manner that modulates neural function. For example, sufficiently stimulating and/or heating at least a portion of a sympathetic nerve can slow or potentially block conduction of neural signals to produce a prolonged or permanent reduction in sympathetic activity. As noted previously, suitable energy modalities can include, for example, RF energy (monopolar and/or bipolar), pulsed RF energy, microwave energy, ultrasound energy (e.g., intravascularly delivered ultrasound, extracorporeal ultrasound, HIFU), laser energy, optical energy, magnetic energy, direct heat, or other suitable energy modalities alone or in combination. Where a system uses a monopolar configuration, a return electrode or ground patch fixed externally on the subject can be used. Moreover, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and incorporated herein by reference in its entirety. Other suitable devices and technologies, such as cryotherapeutic devices, are described in U.S. patent application Ser. No. 13/279,330, filed Oct. 23, 2011, and additional thermal devices are described in U.S. patent application Ser. No. 13/279,205, filed Oct. 21, 2011, each of which are incorporated herein by reference in their entireties.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C. may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures.

In some embodiments, neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. For example, the chemical can be guanethidine, ethanol, phenol, vincristine, a neurotoxin, or another suitable agent selected to alter, damage, or disrupt nerves. In particular embodiment where selective neuromodulation of efferent sympathetic nerve fibers is desirable, a chemical that selectively affects efferent nerve fibers over afferent nerve fibers could be delivered to tissue at the treatment location. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more devices, such as needles originating outside the body or within the vasculature or delivery pumps (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

IV. ACHIEVING INTRAVASCULAR ACCESS TO THE TARGET VESSELS

In accordance with the present technology, neuromodulation of a left and/or right pudendal nerve 40 (FIG. 3), which is intimately associated with a left or right internal pudendal artery 22 (FIG. 2), may be achieved through intravascular access. Further, neuromodulation of a left or right dorsal nerve 30 of the penis 10 (FIGS. 1 and 3), which is intimately associated with left or right internal pudendal artery 22 and/or with a left or right dorsal artery 26 of the penis 10 (FIGS. 1-3), may also be achieved through intravascular access. In yet further embodiments, neuromodulation of an inferior hypogastric plexus, which accompany the branches of a left or right internal iliac artery, may also be achieved through intravascular access. Also in accordance with the present technology, neuromodulation of a left and/or right renal plexus 52, which is intimately associated with a left and/or right renal artery 54, may be achieved through intravascular access.

Figure 6A:
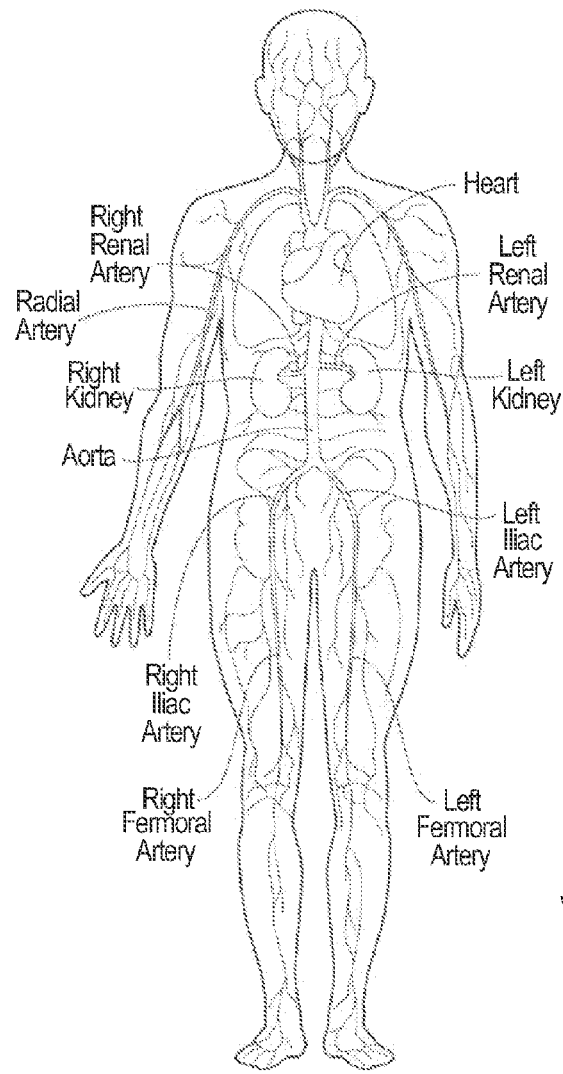
FIGS. 6A and 6B are anatomic views of the arterial vasculature and venous vasculature, respectively, of a human.
Figure 6B:
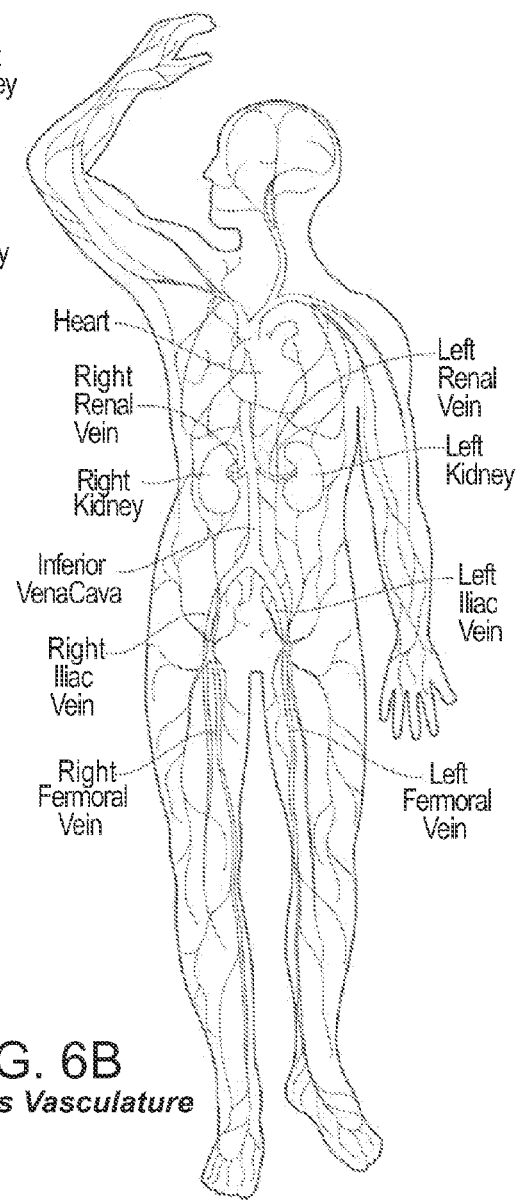

As FIG. 6A shows, blood moved by contractions of the heart is conveyed from the left ventricle of the heart by the aorta. The aorta descends through the thorax and bifurcates at the left and right iliac arteries. The left and right iliac arteries descend, respectively, through the left and right legs and join the left and right femoral arteries. As FIG. 6B shows, the blood collects in veins and returns to the heart, through the femoral veins into the iliac veins and into the inferior vena cava. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter (not shown) may be inserted percutaneously into the left or right femoral artery through this access site, into the respective left or right common iliac artery (FIG. 6A) and down into the internal iliac artery and into the internal pudendal artery 22 (FIG. 2), if desired. This route comprises an intravascular path that offers minimally invasive access to a respective internal iliac artery, internal pudendal artery 22 and/or other penile blood vessels (e.g., dorsal artery 26, cavernous artery 28, etc.). In embodiments that include renal neuromodulation, a catheter may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

Alternatively, the wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the right or left renal arteries 54 (FIGS. 4-6A) or into the right or left common iliac arteries (FIG. 6A) using standard angiographic technique.

V. PROPERTIES AND CHARACTERISTICS OF THE TARGET VASCULATURE

Properties and characteristics of the male reproductive organ vasculature and of the renal vasculature impose challenges to both access and treatment methods, and to system/device designs. Since neuromodulation of the various sympathetic nerve structures innervating the male reproductive viscera (e.g., pudendal nerve perineal nerve, dorsal nerve of the penis, sympathetic nerves derived from the inferior hypogastric plexus, etc.) or kidneys (e.g., renal plexus) may be achieved in accordance with embodiments of the present technology through intravascular access, various aspects of the design of apparatus, systems, and methods for achieving such neuromodulation are disclosed herein. Aspects of the technology disclosed herein address additional challenges associated with variation of physiological conditions and architecture across the patient population and/or within a specific patient across time, as well as in response to disease states, such as hypertension, diabetes, or to conditions associated with penile vasculature (e.g., arthrosclerosis, injury, etc.). For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into the desired vasculature target(s) via a minimally invasive intravascular path. However, minimally invasive arterial or venous access may be challenging, for example, because as compared to some other larger arteries that are routinely accessed using catheters, some of the target arteries (e.g., internal iliac artery, internal pudendal artery, dorsal artery, renal artery, etc.) can be tortuous, may be of relatively small diameter, and/or may require adjustments to the length and flexibility of the catheters. Arterial anatomy also may vary significantly from patient to patient, which further complicates minimally invasive access. Significant inter-patient variation may be seen, for example, in relative tortuosity, diameter, and/or length. Apparatus, systems and methods for achieving neuromodulation via intravascular access can account for these and other aspects of arterial anatomy and its variation across the patient population when minimally invasively accessing an artery. For example, spiral or helical computed tomography (CT) technology can be used to produce 3D images of the vascular features for individual patients, and intravascular path choice as well as device size/diameter, length, flexibility, etc. can be selected based upon the patient's specific vascular features.

In addition to complicated arterial access, specifics of the reproductive or renal anatomy also complicate establishment of stable contact between the neuromodulatory apparatus and a luminal surface or wall of an artery or vein. When the neuromodulatory apparatus includes an energy delivery element, such as an electrode, transducer, heating element or a cryotherapeutic device, consistent positioning and appropriate contact force applied by the energy or cryotherapy delivery element to the vessel wall and adhesion between the applicator and the vessel wall can be important for predictability. However, navigation can be impeded by the tight space within an artery, as well as tortuosity of the artery. Furthermore, establishing consistent contact can be complicated by patient movement, respiration, and/or the cardiac cycle because these factors may cause significant movement of the artery relative to the aorta, for example, and the cardiac cycle may transiently distend the target artery (i.e., cause the wall of the artery to pulse).

To address these challenges, the treatment device or applicator may be designed with relative sizing and flexibility considerations. For example, the artery may have an internal diameter less than approximately 1.7 mm and the treatment device can be delivered using a 3 French, or in some cases, a 4 French sized catheter. In a further example, the renal artery may have an internal diameter in a range of about 2-10 mm and the treatment device can be delivered using a 3, 4, 5, 6, 7 French, or in some cases, an 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a desired target artery and facilitating stable contact between the neuromodulatory apparatus and a luminal surface of the artery, nerves in and around the adventitia of the artery can be modulated via the neuromodulatory apparatus. Effectively applying thermal treatment from within an artery is non-trivial given the potential clinical complications associated with such treatment. For example, the intima and media of the artery are highly vulnerable to thermal injury. As discussed in greater detail below, the intima-media thickness separating the vessel lumen from its adventitia means that target nerves may be multiple millimeters distant (e.g., 1-3 mm) from the luminal surface of the artery. Sufficient energy can be delivered to or heat removed from the target sympathetic nerve fibers to modulate the target nerves without excessively cooling or heating the vessel wall to the extent that the wall is frozen, desiccated, or otherwise potentially affected to an undesirable extent. For example, when employing energy modalities such as RF or ultrasound, energy delivery can be delivered to a location beyond the interior vessel wall. In one embodiment, for example, the majority of the RF or ultrasound energy can be delivered to a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause irreversible damage to the organ, thermal treatment from within the artery can be applied carefully. Accordingly, the complex fluid mechanics and thermodynamic conditions present in the artery during treatment, particularly those that may impact heat transfer dynamics at the treatment site, may be important in applying energy (e.g., heating thermal energy) and/or removing heat from the tissue (e.g., cooling thermal conditions) from within the artery.

The neuromodulatory apparatus can also be configured to allow for adjustable positioning and repositioning of a thermal energy delivery element (e.g., electrode, transducer, cryotherapeutic element or device, etc.) within the artery since location of treatment may also impact clinical efficacy. For example, it may be tempting to apply a full circumferential treatment from within the artery given that the nerves may be spaced circumferentially around an artery. In some situations, a full-circle lesion likely resulting from a continuous circumferential treatment may be potentially related to artery stenosis. Therefore, the formation of more complex lesions along a longitudinal dimension of the artery via the cryotherapeutic devices or other energy delivery elements (e.g., electrodes, transducers, etc.) and/or repositioning of the neuromodulatory apparatus to multiple treatment locations may be desirable. It should be noted, however, that a benefit of forming a circumferential lesion or ablation may outweigh the potential of artery stenosis or the risk may be mitigated with certain embodiments or in certain patients and forming a circumferential lesion or ablation could be a goal. Additionally, variable positioning and repositioning of the neuromodulatory apparatus may prove to be useful in circumstances where the artery is particularly tortuous or where there are proximal branch vessels off the artery main vessel, making treatment in certain locations challenging.

Blood flow through an artery may be temporarily occluded for a short time with minimal or no complications. However, occlusion for a significant amount of time can be avoided in some cases to prevent injury to the organ such as ischemia. It can be beneficial to avoid occlusion altogether or, if occlusion is beneficial, to limit the duration of occlusion (e.g., 2-5 minutes).

VI. METHODS FOR TREATMENT OF ERECTILE DYSFUNCTION

The methods disclosed herein may represent various advantages over a number of conventional approaches and techniques in that they allow for the potential targeting of elevated sympathetic drive, which may either be a cause of ED or a key mediator of the multiple manifestations of the sexual dysfunction problem. In some embodiments, the patient may not be experiencing elevated sympathetic drive; however, neuromodulation may also reduce a parasympathetic threshold for stimulating an erection and/or maintaining an erection. Also, the disclosed methods provide for localized treatment and limited duration treatment regimens (e.g., one-time treatment), thereby reducing long-term treatment compliance issues.

In certain embodiments, the methods provided herein comprise performing penile sympathetic neuromodulation, thereby decreasing penile sympathetic nerve activity for the purposes of being able to develop and/or maintain an erection under parasympathetic stimulation, for example. In other embodiments, the methods provided for renal neuromodulation, thereby reducing systemic sympathetic drive in the patient. Neuromodulation may be repeated one or more times at various intervals until a desired sympathetic nerve activity level or another therapeutic benchmark is reached. In one embodiment, a decrease in sympathetic nerve activity and/or a reduction in a parasympathetic threshold for stimulating an erection and/or maintaining an erection in the patient can be assessed following the neuromodulation treatment procedure. For example, a patient can report, e.g., through self observation or analysis, an improvement in his ability to develop and/or maintain an erection or, in another embodiment, report an increased frequency in ability to develop and/or maintain an erection during arousal (e.g., sexual stimulation/activity).

In another example, a patient can be clinically assessed for ability to develop and/or maintain an erection both before a neuromodulation treatment and following a neuromodulation treatment. Various diagnostic tests for assessing the patient's ability to develop and/or maintain an erection, such as those described above, can be used to assess efficacy of the neuromodulation procedure. For example, the patient can be tested for changes in hormone levels (e.g., testosterone, luteinizing hormone, prolactin and thyroid hormone), vascular blood flow (e.g., such as by magnetic resonance angiography, penile prostaglandin injection followed by duplex ultrasound, etc.), sensory testing (e.g., bulbocavernosus reflex test, penile biothesiometry, etc.), nocturnal penile tumescence and rigidity testing, vascular pressure in the corpora cavernosa (e.g., dynamic infusion cavernosometry, corpus cavernosometry). In another embodiment, a Nerve-Sparing prostatectomy can be performed with a penile plethysmography, which applies a small electrical stimulation to a target nerve and measures the erectile function. In some embodiments, neuromodulation can provide for changes and/or improvement in one or more these diagnostic tests.

In a further embodiment, for example, a decrease in sympathetic nerve activity may be observed via a marker of sympathetic nerve activity in patients experiencing ED, such as decreased levels of plasma norepinephrine (noradrenaline). Other measures or markers of sympathetic nerve activity can include MSNA, norepinephrine spillover, and/or heart rate variability. Additionally, other measurable physiological parameters or markers, such as improved blood pressure control, improved blood glucose regulation, etc., can be used to assess efficacy of the neuromodulation treatment for patients experiencing ED. In one specific example, neuromodulation of target sympathetic nerves in a patient diagnosed with hypertension and erectile dysfunction can reduce the patient's blood pressure (e.g., within about three months to about 12 months post-neuromodulation).

In certain embodiments of the methods provided herein, neuromodulation is expected to result in a change in sympathetic nerve activity over a specific timeframe. For example, in certain of these embodiments, sympathetic nerve activity levels are decreased over an extended timeframe, e.g., within 1 month, 2 months, 3 months, 6 months, 9 months or 12 months post-neuromodulation. In a specific embodiment, a reported number or average number of incidences where a patient reports impotence or premature loss of erection (e.g., premature detumescence), can be decreased by about 5%, about 10%, about 15%, about 20%, about 30%, about 40%, about 50%, about 75%, or about 90%. In other embodiments, patients may report that no ED (e.g., incidence of impotence or premature loss of erection/premature detumescence) is experienced following a neuromodulation procedure.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months or 12 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

Neuromodulation may be performed on a patient experiencing episodes of impotence or having one or more positive diagnosis of ED to improve one or more measurable physiological parameters corresponding to the ED. In certain embodiments of the methods provided herein, the methods are designed to decrease or reduce a patient-perceived or clinician-observed frequency of impotence (e.g., ability to develop an erection) to a target level. In other embodiments, the methods are designed to improve a patient's ability to maintain an erection. In these embodiments, the methods include a step of measuring a frequency and/or quality of ability (e.g., satisfaction with ability) to develop or maintain erection before neuromodulation. In some cases, the pre-neuromodulation frequency can be an average frequency (e.g., averaged over days, weeks, months, years) reported by the patient or observed by a qualified observant (e.g., clinician) using one or more diagnostic tests as described herein. The methods can also include a step of measuring frequency and/or quality of ability to develop or maintain erection using at least one of the methods used pre-neuromodulation to assess frequency and/or quality of ability to develop or maintain erection post-neuromodulation (e.g., 1 month post-treatment, 3 months post-treatment, 6 months post-treatment, 12 months post-treatment, etc.) and comparing the resultant frequency and/or quality to the pre-neuromodulation frequency and/or quality as discussed above. In certain of these embodiments, the treatment is repeated until the target frequency and/or personal satisfaction with ability to develop or maintain erection is reached. In particular embodiments, the post-neuromodulation frequency of impotency is less than the pre-neuromodulation frequency of impotency by an amount greater than about 20%, about 30%, about 50%, about 70%, or about 90%. In other embodiments, the methods are simply designed to decrease frequency of impotence or ED below a desired baseline level without requiring a particular target level.

In some embodiments, reduction of sympathetic activity of target nerves via neuromodulation may also reduce elevated central sympathetic drive. Further, neuromodulation of a target sympathetic nerve may be used to reduce central sympathetic drive in a patient diagnosed with ED. In some embodiments, for example, MSNA can be reduced (e.g., by at least about 10%) in the patient within about three months after at least partially inhibiting sympathetic neural activity in nerves proximate a target blood vessel innervating the penis, or in another embodiment, innervating the kidneys. Similarly, in some instances local norepinephrine spillover to plasma can be reduced (e.g., at least about 20%) in the patient within about three months after at least partially inhibiting sympathetic neural activity in nerves proximate a target blood vessel innervating the penis and/or the kidneys. Additionally, measured local norepinephrine content (e.g., assessed via biopsy, assessed in real-time via intravascular blood collection techniques, etc.) can be reduced (e.g., at least about 5%, 10%, or in another embodiment, by at least 20%) in the patient within about three months after at least partially inhibiting sympathetic neural activity in nerves proximate a target blood vessel innervating the penis and/or the kidneys.

In one prophetic example, a patient diagnosed with ED can be subjected to a baseline assessment indicating a first set of measurable parameters corresponding to the ED. Such parameters can include, for example, frequency of inability to develop an erection, frequency of inability to maintain an erection, testosterone level, blood pressure, cholesterol levels, blood glucose levels, fasting blood insulin levels, and measures of insulin sensitivity. The patient also can be tested (e.g., using nocturnal penile tumescence and rigidity testing) to determine a number of erections during sleep. Following baseline assessment, the patient can be subjected to a penile sympathetic neuromodulation procedure and/or a renal neuromodulation procedure. Such a procedure can, for example, include any of the treatment modalities described herein or another treatment modality in accordance with the present technology. The treatment can be performed on nerves innervating the penile erectile tissue, the skin of the penis or other male reproductive structure, or in other embodiments, on nerves (e.g., afferent or efferent nerve fibers) innervating the kidneys of the patient. Following the treatment (e.g., 1, 3, 6, or 12 months following the treatment), the patient can be subjected to a follow-up assessment. The follow-up assessment can indicate a measurable improvement in one or more physiological parameters corresponding to the ED or other clinical findings (e.g., blood pressure, cholesterol levels, blood glucose levels, fasting blood insulin levels, and measures of insulin sensitivity).

The methods described herein address the sympathetic excess that is thought to be an underlying cause or a central mechanism through which ED affects male patients. In contrast, known therapies currently prescribed for this patient population typically address only specific manifestations of the various sequelae. Additionally, these known therapies can have significant limitations including limited efficacy and/or durability, undesirable side effects and can be subject to adverse or undesirable drug interactions when used in combination. Additionally, conventional therapies require the patient to remain compliant with the treatment regimen over time. In contrast, neuromodulation can be a one-time treatment that would be expected to have durable benefits to improve measurable parameters associated with ED (e.g., ability to develop and/or maintain an erection during sexual arousal and performance), and thereby achieve a favorable patient outcome.

In some embodiments, patients diagnosed with sympathetic overactivity and/or ED can be treated with neuromodulation alone (e.g., penile and/or renal neuromodulation). However, in other embodiments, these patients can be treated with combinations of therapies for treating ED and/or related conditions (e.g., hypertension, diabetes). For example, combinations of therapies can be tailored based on specific manifestations of the condition in a particular patient. In a specific example, patients experiencing ED and having elevated or overactive sympathetic drive and/or presenting hypertension can be treated with both anti-hypertensive therapy (e.g., drugs) and neuromodulation. In another example, neuromodulation can be combined with cholesterol lowering agents (e.g., statins), hormonal therapy (e.g., testosterone therapy), phosphodiesterase type 5 (PDE5) inhibitors (e.g., sildenafil, tadalafil, vardenafil, avanafil, etc.), and/or prostaglandins (e.g., alprostadil) as well as weight loss and lifestyle change recommendations/programs.

Treatment of ED or other conditions relating to or resulting from sympathetic overactivity may refer to preventing ED and/or the other condition(s), slowing the onset or rate of development of ED and/or the other condition(s), reducing the risk of developing ED and/or the other condition(s), preventing or delaying the development of symptoms associated with ED and/or the other condition(s), reducing or ending symptoms associated with ED and/or the other condition(s), generating a complete or partial regression of ED and/or the other condition(s), or some combination thereof.

VII. SELECTED EMBODIMENTS OF NEUROMODULATION SYSTEMS AND DEVICES

Figure 7:
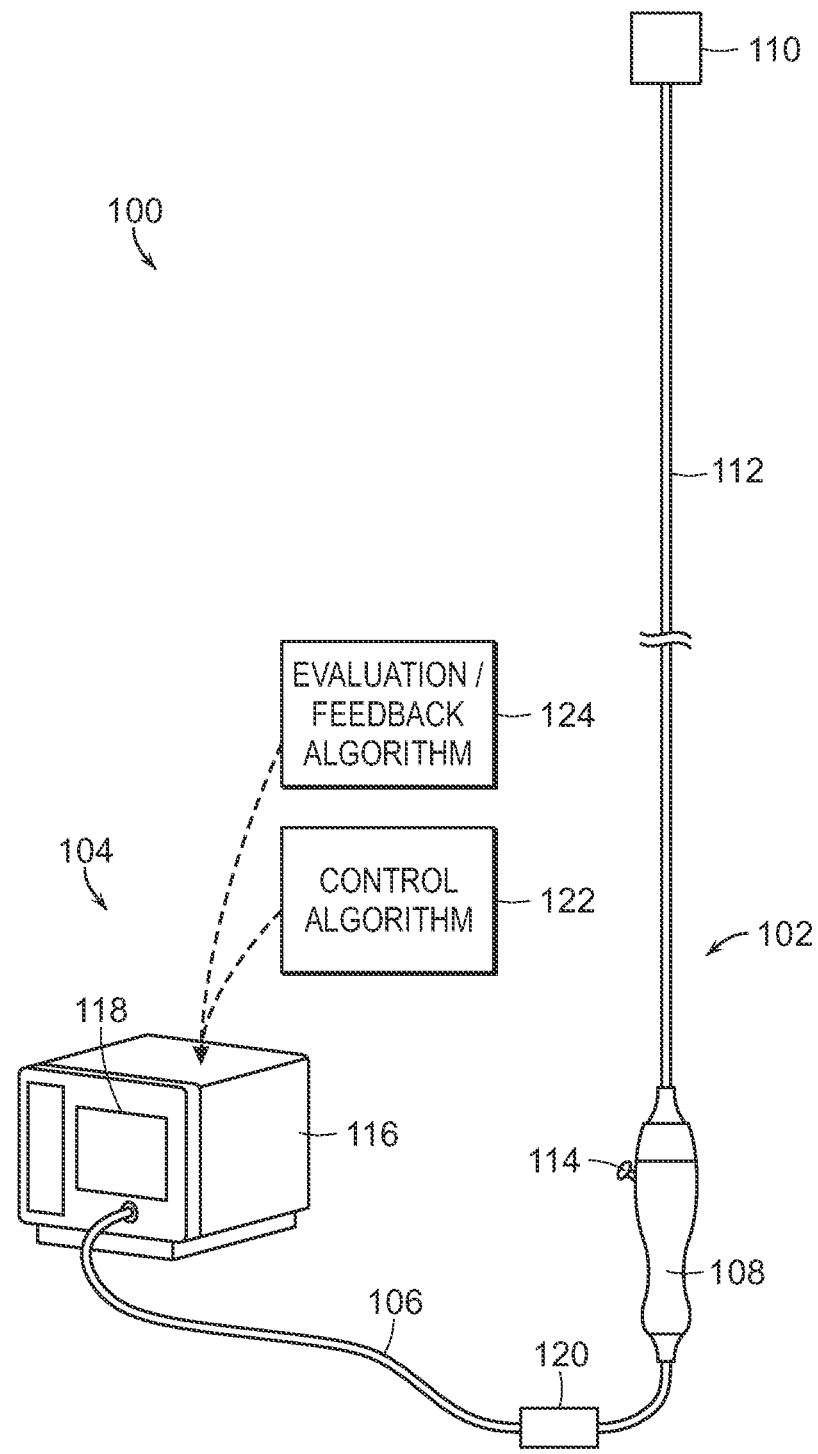
FIG. 7 illustrates an intravascular neuromodulation system configured in accordance with an embodiment of the present technology.

FIG. 7 is a partially schematic diagram illustrating a neuromodulation system 100 ("system 100") configured in accordance with an embodiment of the present technology. The system 100 can include a treatment device 102, an energy source or console 104 (e.g., a RF energy generator, a cryotherapy console, etc.), and a cable 106 extending between the treatment device 102 and the console 104. The treatment device 102 can include a handle 108, a neuromodulation assembly 110, and an elongated shaft 112 extending between the handle 108 and the neuromodulation assembly 110. The shaft 112 can be configured to locate the neuromodulation assembly 110 intravascularly at a treatment location (e.g. internal pudendal artery or internal pudendal vein, a branch of the internal pudendal artery or branch of the internal pudendal vein, the dorsal artery of the penis, the dorsal vein of the penis, an ostium of the dorsal artery, renal artery, an ostium of the renal artery, a renal vein, and/or another suitable structure for the treatment of ED), and the neuromodulation assembly 110 can be configured to provide or support therapeutically-effective neuromodulation at the treatment location. In some embodiments, the shaft 112 and the neuromodulation assembly 110 can be 3, 4, 5, 6, or 7 French or another suitable size. Furthermore, the shaft 112 and the neuromodulation assembly 110 can be partially or fully radiopaque and/or can include radiopaque markers corresponding to measurements, e.g., every 5 cm.

Intravascular delivery can include percutaneously inserting a guide wire (not shown) within the vasculature and moving the shaft 112 and the neuromodulation assembly 110 along the guide wire until the neuromodulation assembly 110 reaches the treatment location. For example, the shaft 112 and the neuromodulation assembly 110 can include a guide-wire lumen (not shown) configured to receive the guide wire in an over-the-wire (OTW) or rapid-exchange (RX) configuration. Other body lumens (e.g., ducts or internal chambers) can be treated, for example, by non-percutaneously passing the shaft 112 and neuromodulation assembly 110 through externally accessible passages of the body or other suitable methods. In some embodiments, a distal end of the neuromodulation assembly 110 can terminate in an atraumatic rounded tip or cap (not shown). The treatment device 102 can also be a steerable or non-steerable catheter device (e.g., a guide catheter) configured for use without a guide wire.

The neuromodulation assembly 110 can have a single state or configuration, or it can be convertible between a plurality of states or configurations. For example, the neuromodulation assembly 110 can be configured to be delivered to the treatment location in a delivery state and to provide or support therapeutically-effective neuromodulation in a deployed state. In these and other embodiments, the neuromodulation assembly 110 can have different sizes and/or shapes in the delivery and deployed states. For example, the neuromodulation assembly 110 can have a low-profile configuration in the delivery state and an expanded configuration in the deployed state. In another example, the neuromodulation assembly 110 can be configured to deflect into contact with a vessel wall in a delivery state. The neuromodulation assembly 110 can be converted (e.g., placed or transformed) between the delivery and deployed states via remote actuation, e.g., using an actuator 114 of the handle 108. The actuator 114 can include a knob, a pin, a lever, a button, a dial, or another suitable control component. In other embodiments, the neuromodulation assembly 110 can be transformed between the delivery and deployed states using other suitable mechanisms or techniques.

In some embodiments, the neuromodulation assembly 110 can include an elongated member (not shown) that can be configured to curve (e.g., arch) in the deployed state, e.g., in response to movement of the actuator 114. For example, the elongated member can be at least partially helical/spiral in the deployed state. In other embodiments, the neuromodulation assembly 110 can include a balloon (not shown) that can be configured to be at least partially inflated in the deployed state. An elongated member, for example, can be well suited for carrying one or more heating elements, electrodes or transducers and for delivering direct heat, electrode-based or transducer-based treatment. A balloon, for example, can be well suited for containing refrigerant (e.g., during or shortly after liquid-to-gas phase change) and for delivering cryotherapeutic treatment. A balloon can also be used in some embodiments for carrying suitable RF conducting electrodes. In some embodiments, the neuromodulation assembly 110 can be configured for intravascular and/or transvascular delivery of chemicals. For example, the neuromodulation assembly 110 can include one or more openings (not shown), and chemicals (e.g., drugs or other agents) can be deliverable through the openings. For transvascular delivery, the neuromodulation assembly 110 can include one or more needles (not shown) (e.g., retractable needles) and the openings can be at end portions of the needles.

The console 104 is configured to control, monitor, supply, or otherwise support operation of the treatment device 102. In some embodiments, the console 104 can be separate from and in communication with the treatment device 102. In other embodiments, the console 104 can be contained within or be a component of the treatment device 102. In still further embodiments, the treatment device 102 can be self-contained and/or otherwise configured for operation without connection to the console 104. As shown in FIG. 3, the console 104 can include a primary housing 116 having a display 118. The system 100 can include a control device 120 along the cable 106 configured to initiate, terminate, and/or adjust operation of the treatment device 102 directly and/or via the console 104. In other embodiments, the system 100 can include another suitable control mechanism. For example, the control device 120 can be incorporated into the handle 108. The console 104 can be configured to execute an automated control algorithm 122 and/or to receive control instructions from an operator. Furthermore, the console 104 can be configured to provide feedback to an operator before, during, and/or after a treatment procedure via the display 118 and/or an evaluation/feedback algorithm 124. In some embodiments, the console 104 can include a processing device (not shown) having processing circuitry, e.g., a microprocessor. The processing device can be configured to execute stored instructions relating to the control algorithm 122 and/or the evaluation/feedback algorithm 124. Furthermore, the console 104 can be configured to communicate with the treatment device 102, e.g., via the cable 106. For example, the neuromodulation assembly 110 of the treatment device 102 can include a sensor (not shown) (e.g., a recording electrode, a temperature sensor, a pressure sensor, or a flow rate sensor) and a sensor lead (not shown) (e.g., an electrical lead or a pressure lead) configured to carry a signal from the sensor to the handle 108. The cable 106 can be configured to carry the signal from the handle 108 to the console 104.

The console 104 can have different configurations depending on the treatment modality of the treatment device 102. For example, when the treatment device 102 is configured for electrode-based or transducer-based treatment, the console 104 can include an energy generator (not shown) configured to generate RF energy, pulsed RF energy, microwave energy, optical energy, ultrasound energy (e.g., intravascularly delivered ultrasound, extracorporeal ultrasound, HIFU), magnetic energy, direct heat energy, or another suitable type of energy. In some embodiments, for example, the console 104 can include a RF generator operably coupled to one or more electrodes (not shown) of the neuromodulation assembly 110.

When the treatment device 102 is configured for cryotherapeutic treatment, the console 104 can include a refrigerant reservoir (not shown) and can be configured to supply the treatment device 102 with refrigerant, e.g., pressurized refrigerant in liquid or substantially liquid phase. Similarly, when the treatment device 102 is configured for chemical-based treatment, the console 104 can include a chemical reservoir (not shown) and can be configured to supply the treatment device 102 with one or more chemicals. In some embodiments, the treatment device 102 can include an adapter (not shown) (e.g., a luer lock) configured to be operably coupled to a syringe (not shown). The adapter can be fluidly connected to a lumen (not shown) of the treatment device 102, and the syringe can be used, for example, to manually deliver one or more chemicals to the treatment location, to withdraw material from the treatment location, to inflate a balloon (not shown) of the neuromodulation assembly 110, to deflate a balloon of the neuromodulation assembly 110, or for another suitable purpose. In other embodiments, the console 104 can have other suitable configurations.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VIII. SELECTED EXAMPLES OF TREATMENT PROCEDURES FOR NEUROMODULATION

Referring back to FIG. 5, which illustrates modulating renal nerves with a treatment device 60 having a number of features similar to the treatment device 102 of the system 100 (FIG. 7). The treatment device 60 provides access to the renal plexus 52 through an intravascular path P, such as a percutaneous access site in the femoral (illustrated), brachial, radial, or axillary artery to a targeted treatment site within a respective renal artery 54. As illustrated, a section of the proximal portion 64 of the shaft 62 is exposed externally of the patient. By manipulating the proximal portion 64 of the shaft 62 from outside the intravascular path P, the clinician may advance the shaft 62 through the sometimes tortuous intravascular path P and remotely manipulate the distal portion 66 of the shaft 62. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 60. In some embodiments, the shaft 62 and the therapeutic element 68 can be 3, 4, 5, 6, or 7 French or another suitable size. As discussed, the shaft 62 and the therapeutic element 68 can be partially or fully radiopaque and/or can include radiopaque markers corresponding to measurements, e.g., every 5 cm.

Referring back to FIGS. 1-5 together and in some embodiments, the therapeutic element 68, for example, can be configured to radially expand into a deployed state at a pre-selected treatment location (e.g. internal pudendal artery or internal pudendal vein, a branch of the internal pudendal artery or branch of the internal pudendal artery vein, the dorsal artery of the penis, the dorsal vein of the penis, an ostium of the dorsal artery, renal artery, an ostium of the renal artery, a renal vein, and/or another suitable structure for the treatment of ED). In the deployed state, the therapeutic element 68 can be configured to contact an inner wall of a vessel of the target vasculature and to form a suitable lesion or pattern of lesions without the need for repositioning. For example, the therapeutic element 68 can be configured to form a single lesion or a series of lesions, e.g., overlapping or non-overlapping. In some embodiments, the lesion or pattern of lesions can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the therapeutic element 68 can be configured form a partially-circumferential lesion or a fully-circumferential lesion at a single longitudinal segment or zone of the vessel. During treatment, the therapeutic element 68 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the therapeutic element 68 can be configured to cause therapeutically-effective neuromodulation (e.g., using ultrasound energy) without contacting a vessel wall.

A variety of other suitable treatment locations are also possible in and around the target artery, the target vein, and/or other suitable structures. In a specific example, since the internal pudendal arteries 22 become narrower and more tortuous further from the internal iliac artery, it can be more convenient in some cases to treat an internal pudendal artery 22 at its trunk. Furthermore, a treatment procedure can include treatment at any suitable number of treatment locations, e.g., a single treatment location, two treatment locations, or more than two treatment locations. In some embodiments, different treatment locations can correspond to different portions of the target artery, the target vein, and/or other suitable structures proximate tissue having relatively high concentrations of targeted sympathetic nerves. The shaft 62 can be steerable (e.g., via one or more pull wires, a steerable guide or sheath catheter, etc.) and can be configured to move the therapeutic element 68 between treatment locations. At each treatment location, the therapeutic element 68 can be activated to cause modulation of nerves proximate the treatment location. Activating the therapeutic element 68 can include, for example, heating, cooling, stimulating, or applying another suitable treatment modality at the treatment location. Activating the therapeutic element 68 can further include applying various energy modalities at varying power levels, intensities and/or for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the therapeutic element 68 can be configured to introduce (e.g., inject) a chemical (e.g., a drug or other agent) into target tissue at the treatment location. Such chemicals or agents can be applied at various concentrations depending on treatment location and the relative depth of the target nerves.

The therapeutic element 68 can be positioned at a treatment location within the target artery, for example, via a catheterization path including a femoral artery and the aorta to the renal artery, or in another embodiment, a catheterization path including the internal iliac artery and the internal pudendal artery, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The therapeutic element 68 can be configured to accommodate the anatomy of the target artery, the target vein, and/or another suitable structure. For example, the therapeutic element 68 can include a balloon (not shown) configured to inflate to a size generally corresponding to the internal size of the target artery, the target vein, and/or another suitable structure. In some embodiments, the therapeutic element 68 can be an implantable device and a treatment procedure can include locating the therapeutic element 68 at the treatment location using the shaft 62 fixing the therapeutic element 68 at the treatment location, separating the therapeutic element 68 from the shaft 62, and withdrawing the shaft 62. Other treatment procedures for modulation of target sympathetic nerves in accordance with embodiments of the present technology are also possible.

Figure 8:
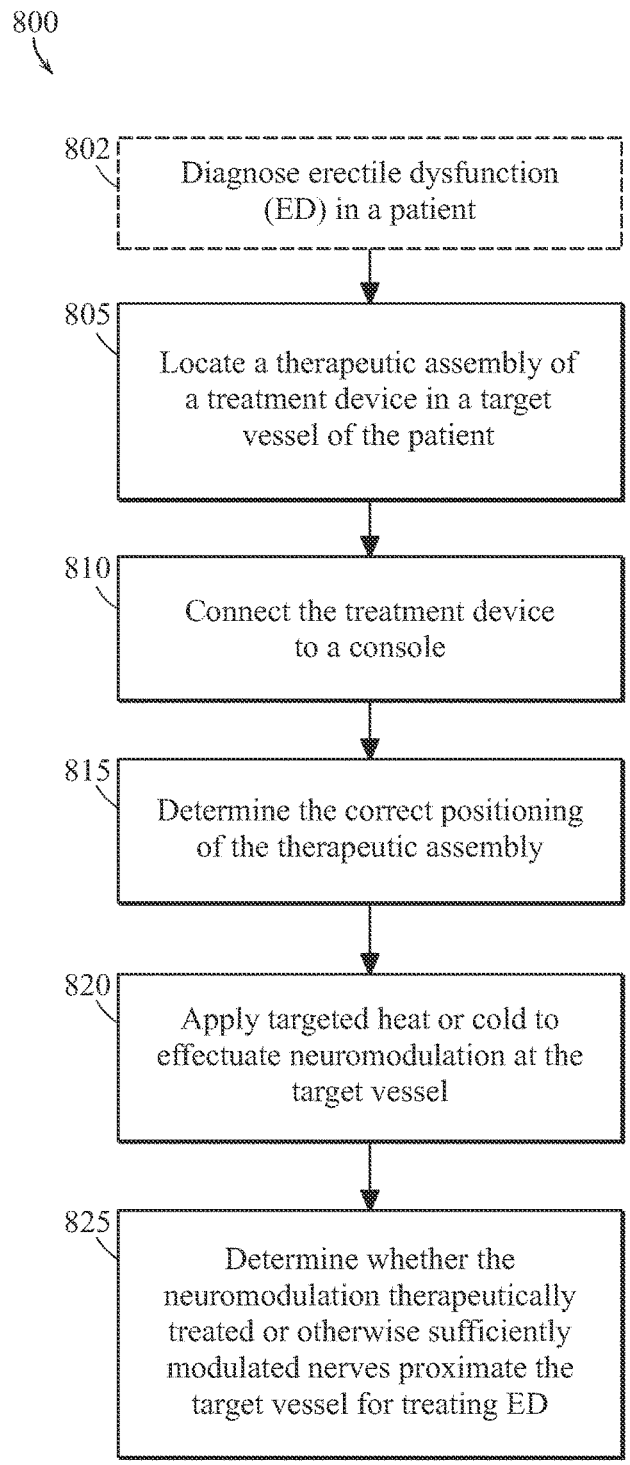
FIG. 8 is a block diagram illustrating a method of modulating target sympathetic nerves in accordance with an embodiment of the present technology.

FIG. 8 is a block diagram illustrating a method 800 of modulating sympathetic nerves using the system 100 described above with reference to FIG. 7 or another suitable system. With reference to FIGS. 1-4 and 6A-8 together, the method 800 can optionally include diagnosing ED in a patient (if not yet determined) and/or selecting a suitable patient for performing neuromodulation (block 802). The method 800 can include intravascularly locating the neuromodulation assembly 110 in a delivery state (e.g., low-profile configuration) at a first target site in or near a target blood vessel (e.g., an internal pudendal artery or internal pudendal vein, dorsal artery or dorsal vein of the penis, an internal iliac artery or internal iliac vein, a renal artery or renal vein, and/or another suitable structure) (block 805). The treatment device 102 and/or portions thereof (e.g., the neuromodulation assembly 110) can be inserted into a guide catheter or sheath to facilitate intravascular delivery of the neuromodulation assembly 110. In certain embodiments, for example, the treatment device 102 can be configured to fit within an 8 Fr guide catheter or smaller (e.g., 7 Fr, 6 Fr, 5 Fr, 4 Fr, 3 Fr, etc.) to access small peripheral vessels. A guide wire (not shown), if present, can be used to manipulate and enhance control of the shaft 112 and the neuromodulation assembly 110 (e.g., in an over-the-wire or a rapid-exchange configuration). In some embodiments, radiopaque markers and/or markings on the treatment device 102 and/or the guide wire can facilitate placement of the neuromodulation assembly 110 at the target site (e.g., a target vessel of a patient with ED). In some embodiments, a contrast material can be delivered distally beyond the neuromodulation assembly 110, and fluoroscopy and/or other suitable imaging techniques can be used to aid in placement of the neuromodulation assembly 110 at the target site.

The method 800 can further include connecting the treatment device 102 to the console 104 (block 810), and determining whether the neuromodulation assembly 110 is in the correct position at the target site and/or whether the neuromodulation assembly (e.g., electrodes or cryotherapy balloon) is functioning properly (block 815). Once the neuromodulation assembly 110 is properly located at the target site and no malfunctions are detected, the console 104 can be manipulated to initiate application of an energy field to the target site to cause electrically-induced and/or thermally-induced modulation of target sympathetic nerves near the target vessel (e.g., using electrodes, transducers, direct heat application or cryotherapeutic devices). Accordingly, heating and/or cooling of the neuromodulation assembly 110 causes modulation of sympathetic nerves at the target site to reduce or diminish transmitting signals via sympathetic nerve fibers associated with the target site (block 820). In some embodiments, the target vessel can be a first target vessel (e.g., a first renal artery, a first internal pudendal artery, a first dorsal artery, etc.) and the treatment procedure can include modulating nerves associated with a second target vessel (e.g., a second renal artery, a second internal pudendal artery, a second dorsal artery, etc.). In one embodiment, the first target vessel could be a first renal artery and the second target vessel could be a second renal artery. In another embodiment, the first target vessel could be an internal pudendal artery or dorsal artery and second target vessel could be a renal artery.

In one example, the treatment device 102 can be an RF energy emitting device and RF energy can be delivered through energy delivery element(s) or electrode(s) to one or more locations along the inner wall of the target vessel for predetermined periods of time (e.g., 120 seconds). In some embodiments, multiple treatments (e.g., 4-6) may be administered in multiple target vessel locations to achieve a desired coverage. An objective of a treatment may be, for example, to heat tissue to a desired depth (e.g., at least about 3 mm, about 1 mm, 2, mm, etc.) to a temperature (e.g., about 65° C.) that would modulate one or more nerve fibers associated with or adjacent to one or more lesions formed in the vessel wall. A clinical objective of the procedure typically is to neuromodulate a sufficient number of sympathetic nerves (either efferent or afferent nerves) to reduce or diminish transmitting signals and/or to cause a reduction in central sympathetic activity or in sympathetic tone or drive to the penis (e.g., penile erectile tissue). If the objective of a treatment is met (e.g., tissue is heated to about 65° C. to a depth of about 1-3 mm) the probability of modulating or affecting nerve tissue (e.g., altering nerve function) is high. In some embodiments, a single neuromodulation treatment procedure can provide for sufficient modulation of target sympathetic nerves (e.g., modulation of a sufficient number of nerve fibers) to provide a desired clinical outcome. In other embodiments, more than one treatment may be beneficial for modulating a desired number or volume of target sympathetic nerve fibers, and thereby achieve clinical success. In other embodiments, an objective may include reducing or eliminating target sympathetic nerve function completely.

In a specific example of using RF energy for sympathetic nerve modulation, a clinician can commence treatment which causes the control algorithm 122 (FIG. 7) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time, i.e., in a linear manner. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts, or in a further embodiment, $P_{MAX}$ is 6.5 watts. In some embodiments, $P_{MAX}$ can be about 6 watts to about 10 watts. Optionally, the power may be maintained at the maximum power $P_{MAX}$ for a desired period of time or up to the desired total treatment time (e.g., up to about 120 seconds) or until a specified temperature is reached or maintained for a specified time period.

In another specific example, the treatment device 102 can be a cryogenic device and cryogenic cooling can be applied for one or more cycles (e.g., for 30 second increments, 60 second increments, 90 second increments, etc.) in one or more locations along the circumference and/or length of the target vessel. The cooling cycles can be, for example, fixed periods or can be fully or partially dependent on detected temperatures (e.g., temperatures detected by a thermocouple (not shown) of the neuromodulation assembly 110). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

In another example, neuromodulation of sympathetic nerves innervating the penis, for example, can be accomplished with extracorporeally-delivered energy (e.g., extracorporeal ultrasound). In one embodiment, for example, the energy may be delivered through the dorsal skin of the penis to modulate the dorsal nerve 30 of the penis 10 (FIGS. 1 and 3).

After providing the therapeutically-effective neuromodulation energy (e.g., cryogenic cooling, direct heating, RF energy, ultrasound energy, etc.), the method 800 may also include determining whether the neuromodulation therapeutically treated the patient for ED or otherwise sufficiently modulated nerves or other neural structures proximate the target site(s) for treating ED or otherwise affected the patient's ability to develop and/or maintain an erection (block 825). For example, the process of determining whether the neuromodulation therapeutically treated the nerves can include determining whether nerves were sufficiently modulated or otherwise disrupted to reduce, suppress, inhibit, block or otherwise affect the afferent and/or efferent signals (e.g., to the kidneys, to the penis, etc.). For example, evaluation of suitable biomarkers, stimulation and recording of nerve signals, etc. can be used to assess sympathetic activity of the nerves. For renal neuromodulation, for example, suitable biomarkers and their detection are described in U.S. Provisional Patent Application No. 61/608,625, filed Mar. 8, 2012, and U.S. Provisional Patent Application No. 61/746,528, filed Dec. 27, 2012, both of which are incorporated herein by reference in their entireties. Other suitable devices and technologies, such as endovascular intraoperative renal nerve monitoring devices are described in International Patent Application No. PCT/US12/63759, filed Jan. 29, 2013, and incorporated herein by reference in its entirety. In a further embodiment, patient assessment could be performed at time intervals (e.g., 1 month, 3 months, 6 months, 12 months) following neuromodulation treatment. For example, the patient can be assessed for ability to obtain erection while sleeping, e.g., by using nocturnal penile tumescence, and measures of sympathetic activity (e.g., MSNA, and/or norepinephrine spillover to plasma, whole body norepinephrine spillover, and heart rate variability). Further evaluation could include assessment of the patient's health, including assessment of improvement of other health related factors affecting some ED patients, (e.g., blood pressure, sodium level, insulin sensitivity, etc). Additional evaluation could include a patient's self-assessment, for example, a reporting of ability, or increased frequency in ability to develop and/or maintain an erection.

In other embodiments, various steps in the method 800 can be modified, omitted, and/or additional steps may be added. In further embodiments, the method 800 can have a delay between applying therapeutically-effective neuromodulation energy at a first target site at or near a first target vessel and applying therapeutically-effective neuromodulation energy at a second target site at or near a second target vessel. For example, neuromodulation of the first target vessel (e.g., a first internal pudendal artery) can take place at a first treatment session, and neuromodulation of the second target vessel (e.g., a second internal artery) can take place a second treatment session at a later time.

As discussed previously, treatment procedures for modulation of sympathetic nerves in accordance with embodiments of the present technology are expected to improve at least one aspect associated with ED (e.g., the ability develop and/or maintain an erection) or other sexual dysfunction problem (e.g., low libido). For example, with respect to ED, modulation of sympathetic nerves at an appropriate target vessel as disclosed herein and in accordance with embodiments of the present technology is expected to improve the patient's ability, or increased frequency in ability, to develop and/or maintain an erection sufficient, for example, satisfactory sexual intercourse. In a particular example, the ability of a patient to develop an erection during sexual stimulation or activity is expected to be increased at least about 5% within about three months after modulating the sympathetic nerves innervating the penis, e.g., the penile erectile tissue in the patient, or the renal sympathetic nerves (e.g., for reducing central sympathetic activity) that is believed to contribute to various aspects of the ED problem. With respect to central sympathetic activity (e.g., overactivity or hyperactivity), for example, modulation of renal nerves is expected to reduce MSNA and/or whole body norepinephrine spillover in patients. These and other clinical effects are expected to be detectable immediately after a treatment procedure or after a delay, e.g., of 1, 2, or 3 months. In some instances, it may be useful to repeat neuromodulation at the same treatment location or a different treatment location after a suitable delay, e.g., 1, 2, or 3 years. In still other embodiments, however, other suitable treatment regimens or techniques may be used.

IX. PERTINENT ANATOMY AND PHYSIOLOGY

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with sympathetic neuromodulation.

A. The Sympathetic Nervous System

The SNS is a branch of the autonomic nervous system along with the enteric nervous system and parasympathetic nervous system. It is always active at a basal level (called sympathetic tone) and becomes more active during times of stress. Like other parts of the nervous system, the SNS operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine binds adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The SNS is responsible for up- and down-regulation of many homeostatic mechanisms in living organisms. Fibers from the SNS innervate tissues in almost every organ system, providing at least some regulatory function to physiological features as diverse as pupil diameter, gut motility, and urinary output. This response is also known as the symnpatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the SNS and indirectly via catecholamines secreted from the adrenal medulla.

Science typically looks at the SNS as an automatic regulation system, that is, one that operates without the intervention of conscious thought. Some evolutionary theorists suggest that the SNS operated in early organisms to maintain survival as the SNS is responsible for priming the body for action. One example of this priming is in the moments before waking, in which sympathetic outflow spontaneously increases in preparation for action.

1. The Sympathetic Chain

Figure 9:
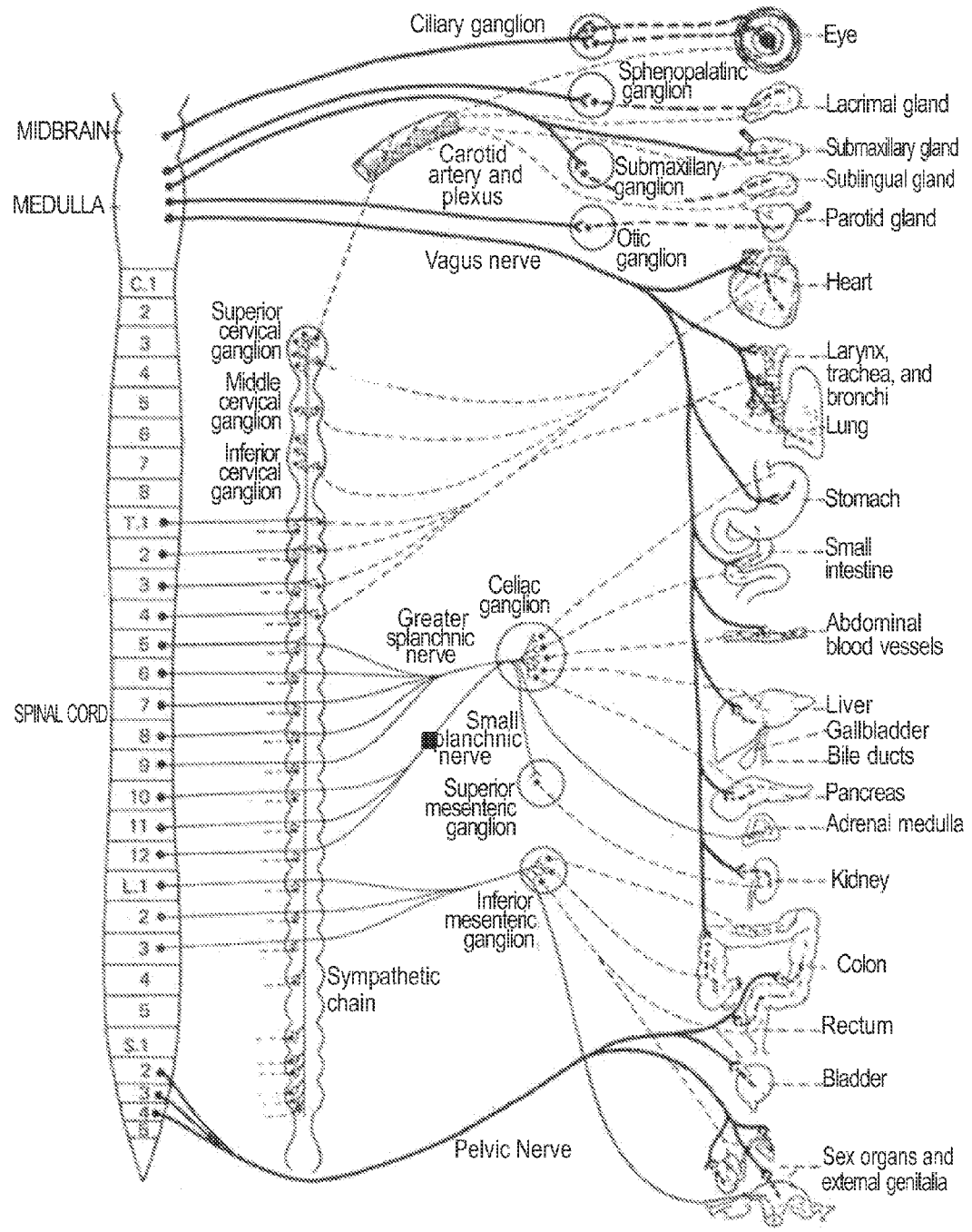
FIG. 9 is a conceptual illustration of the sympathetic nervous system (SNS) and how the brain communicates with the body via the SNS.

As shown in FIG. 9, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors that connect to either the paravertebral (which lie near the vertebral column) or prevertebral (which lie near the aortic bifurcation) ganglia extending alongside the spinal column.

In order to reach the target organs and glands, the axons travel long distances in the body. Many axons relay their message to a second cell through synaptic transmission. The first cell (the presynaptic cell) sends a neurotransmitter across the synaptic cleft (the space between the axon terminal of the first cell and the dendrite of the second cell) where it activates the second cell (the postsynaptic cell). The message is then propagated to the final destination.

In the SNS and other neuronal networks of the peripheral nervous system, these synapses are located at sites called ganglia, discussed above. The cell that sends its fiber to a ganglion is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands. The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Sympathetic Neural Activity

Messages travel through the SNS in a bidirectional flow. Efferent messages may trigger changes in different parts of the body simultaneously. For example, the SNS may accelerate heart rate; widen bronchial passages; decrease motility (movement) of the large intestine; constrict blood vessels; increase peristalsis in the esophagus; cause pupil dilation, cause piloerection (i.e., goose bumps), cause perspiration (i.e., sweating), and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the RAAS has been a longstanding, but somewhat ineffective, approach for reducing overactivity of the SNS.

Some experimental data and clinical results are suggestive of the role the sympathetic nervous system has as a contributor to ED. For example, detumescence by sympathetic trunk stimulation was determined experimentally in canine studies. Moreover, these studies also demonstrated that stimulation of the sympathetic trunk prevented erection entirely, despite simultaneous stimulation of the parasympathetic nerves (e.g., the cavernous nerves) of the penis. Additional evidence suggests that hypertension and ED are related conditions. For example, disturbance of endothelium-derived factors (e.g., endothelium-derived hyperpolarizing factor, endothelium-derived relaxing factor, NO) can lead to an increase in VSM contraction which systemically can cause hypertension, and locally (e.g., in the penis) can prevent dilation of the arteries (e.g., the coiled helicine arteries) supplying the corpora cavernosa and corpus spogniosum, thereby preventing erection.

(i) Renal Sympathetic Efferent Nerve Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 10A:
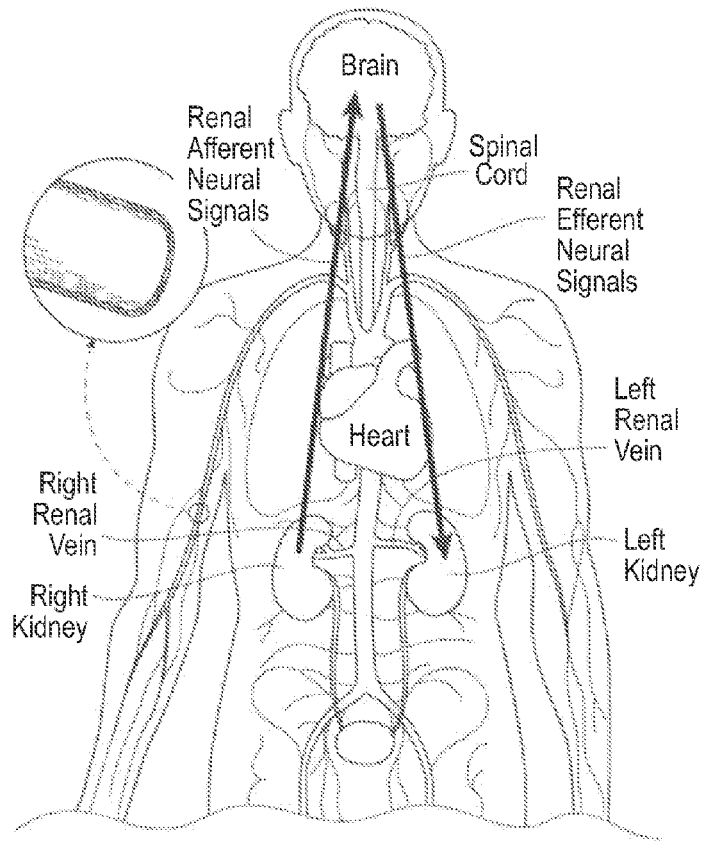
FIGS. 10A and 10B are anatomic and conceptual views, respectively, of a human body depicting neural efferent and afferent communication between the brain and kidneys.
Figure 10B:
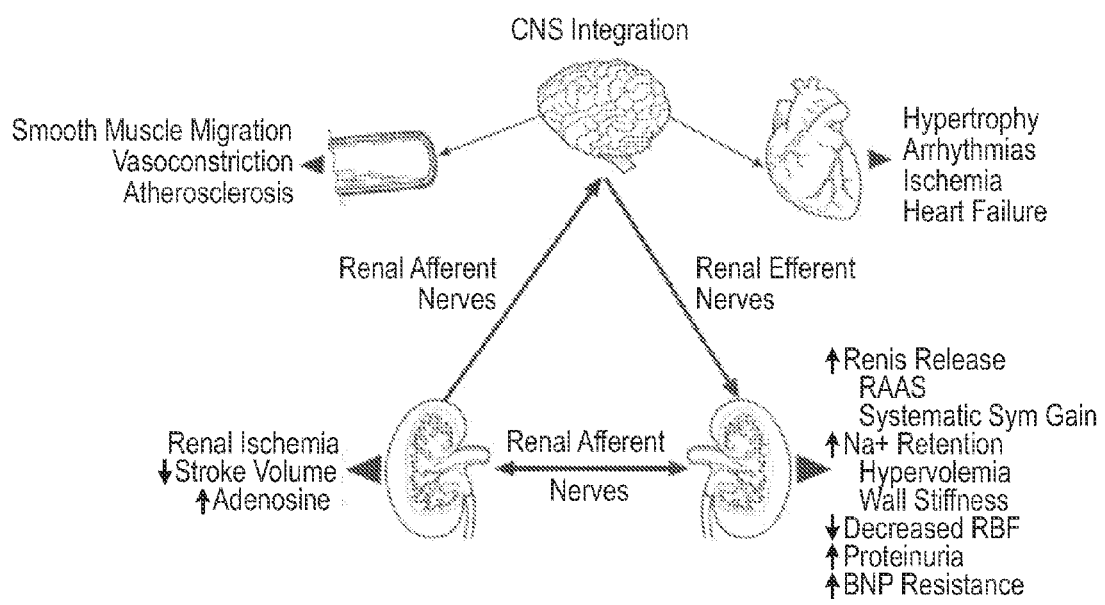

The kidneys communicate with integral structures in the CNS via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10A and 10B, this afferent communication might be from the kidney to the brain or might be from one kidney to the other kidney (via the CNS). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and renal blood flow, and (ii) modulation of tissue with afferent sensory nerves will reduce the systemic contribution to hypertension and other disease states (e.g., sexual dysfunction, ED) associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

X. TREATMENT EXAMPLES

Effect of Renal Neuromodulation on Hypertension

Patients were selected having a baseline systolic blood pressure of 160 mm Hg or more (≥150 mm Hg for patients with type 2 diabetes) and taking three or more antihypertensive drugs, and were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, p<0.0001), whereas they did not differ from baseline in the control group (change of 1/0 mm Hg, baseline of 178/97 mm Hg, p=0.77 systolic and p=0.83 diastolic). Between-group differences in blood pressure at 6 months were 33/11 mm Hg (p<0.0001). At 6 months, 41 (84%) of 49 patients who underwent renal neuromodulation had a reduction in systolic blood pressure of 10 mm Hg or more, compared with 18 (35%) of 51 control patients (p<0.0001).

XI. FURTHER EXAMPLES

1. A method of treating a human patient diagnosed with erectile dysfunction, the method comprising:
   intravascularly positioning a neuromodulation assembly within a target blood vessel of the patient and adjacent to target sympathetic nerve of the patient; and
   reducing sympathetic neural activity in the patient by delivering energy to the target sympathetic nerve via the neuromodulation assembly to modulate the target sympathetic nerve,
   wherein reducing sympathetic neural activity improves a measurable physiological parameter corresponding to the erectile dysfunction of the patient.

2. The method of example 1 wherein reducing sympathetic neural activity in the patient in a manner that improves a measurable physiological parameter corresponding to the erectile dysfunction comprises increasing a frequency of penile erections in the patient.

3. The method of example 2 wherein increasing a frequency of penile erections in the patient is self-reported by the patient within about three months to about 12 months after reducing sympathetic neural activity in the patient.

4. The method of example 2 or example 3 wherein increasing a frequency of penile erections is assessed using a nocturnal penile tumescence test.

5. The method of any one of examples 1-4 wherein reducing sympathetic neural activity in the patient in a manner that improves a measurable physiological parameter corresponding to the erectile dysfunction comprises improving a result on one or more of a penile vascular flow test, a penile rigidity test, a vascular pressure test, and a penile nerve sensory test.

6. The method of any one of examples 1-5 wherein reducing sympathetic neural activity in the patient in a manner that improves a measurable physiological parameter corresponding to the erectile dysfunction comprises reducing a number of incidences where the patient reports impotence or premature loss of erection by at least about 20%.

7. The method of any one of examples 1-6 wherein reducing sympathetic neural activity in the patient in a manner that improves a measurable physiological parameter corresponding to the erectile dysfunction comprises reducing an average patient-perceived or clinician-observed frequency of impotence or premature detumescence during sexual activity within about three months to about 12 months after reducing sympathetic neural activity in the patient.

8. The method of any one of examples 1-7 wherein reducing sympathetic neural activity in the patient in a manner that improves a measurable physiological parameter corresponding to the erectile dysfunction comprises reducing muscle sympathetic nerve activity (MSNA) in the patient.

9. The method of any one of examples 1-8 wherein reducing sympathetic neural activity in the patient in a manner that improves a measurable physiological parameter corresponding to the erectile dysfunction comprises reducing whole body norepinephrine spillover in the patient.

10. The method of any one of examples 1-9 wherein reducing sympathetic neural activity in the patient in a manner that improves a measurable physiological parameter corresponding to the erectile dysfunction comprises reducing a parasympathetic threshold for stimulating an erection and/or maintaining an erection in the patient.

11. The method of any one of examples 1-10 wherein the patient is diagnosed with hypertension, and wherein reducing sympathetic neural activity in the patient further results in a therapeutically beneficial reduction in blood pressure of the patient.

12. The method of any one of examples 1-11 wherein reducing sympathetic neural activity in the patient by delivering energy to the target sympathetic nerve comprises selectively neuromodulating efferent penile nerves in the patient compared to afferent penile nerves in the patient.

13. The method of any one of examples 1-12 wherein reducing sympathetic neural activity in the patient by delivering energy to the target sympathetic nerve comprises at least partially inhibiting penile sympathetic efferent neural activity.

14. The method of any one of examples 1-13 wherein reducing sympathetic neural activity in the patient by delivering energy to the target sympathetic nerve comprises thermally modulating the target sympathetic nerve of the patient via an intravascularly positioned catheter carrying the neuromodulation assembly.

15. The method of example 14 wherein thermally modulating the target sympathetic nerve comprises at least partially ablating the target sympathetic nerve via the neuromodulation assembly.

16. The method of example 14 wherein thermally modulating the target sympathetic nerve comprises cryotherapeutically cooling the target sympathetic nerve.

17. The method of example 14 wherein thermally modulating the target sympathetic nerve comprises heating the target sympathetic nerve.

18. The method of any one of examples 1-17 wherein intravascularly positioning a neuromodulation assembly within a target blood vessel of the patient includes positioning a neuromodulation assembly within an internal pudendal artery.

19. The method of any one of examples 1-17 wherein intravascularly positioning a neuromodulation assembly within a target blood vessel of the patient includes positioning a neuromodulation assembly within a dorsal artery of a penis.

20. The method of any one of examples 1-17 wherein intravascularly positioning a neuromodulation assembly within a target blood vessel of the patient includes positioning a neuromodulation assembly within an internal iliac artery.

21. The method of any one of examples 1-17 wherein intravascularly positioning a neuromodulation assembly within a target blood vessel of the patient includes positioning a neuromodulation assembly within a renal artery.

22. The method of any one of examples 1-20 wherein reducing sympathetic neural activity in the patient by delivering energy to the target sympathetic nerve includes reducing sympathetic neural activity in one or more sympathetic nerves innervating penile erectile tissue of the patient.

23. The method of any one of examples 1-17 wherein reducing sympathetic neural activity in the patient by delivering energy to the target sympathetic nerve includes reducing sympathetic neural activity in one or more sympathetic nerves innervating a kidney of the patient.

24. A method, comprising:
introducing a neuromodulation assembly at a distal portion of a treatment device proximate to neural fibers innervating penile tissue of a human patient diagnosed with erectile dysfunction or low libido;
partially disrupting function of the neural fibers innervating the penile tissue by applying thermal energy to the neural fibers via the neuromodulation assembly; and
removing the neuromodulation assembly from the patient after treatment,
wherein partial disruption of the function of the neural fibers innervating the penile tissue therapeutically treats the diagnosed erectile dysfunction or low libido.

25. The method of example 24 wherein the neuromodulation assembly is introduced percutaneously.

26. The method of example 24 wherein introducing a neuromodulation assembly at a distal portion of a treatment device proximate to neural fibers innervating penile tissue of a human patient comprises extracorporeally positioning the neuromodulation assembly on penile tissue, and wherein applying thermal energy to the neural fibers via the neuromodulation assembly comprises applying thermal energy through penile skin.

27. The method of any one of examples 24-26 wherein the neural fibers innervating the penile tissue comprise the dorsal nerve of the penis.

28. The method of example 24 wherein the patient is diagnosed with low libido, and wherein partial disruption of the function of the neural fibers reverses low libido in the patient.

29. A method for treating erectile dysfunction in a human patient, the method comprising:
transluminally positioning an energy delivery element of a catheter within a target blood vessel of the patient and adjacent to neural fibers that innervate a kidney or penile tissue of the patient; and
at least partially ablating the neural fibers innervating the kidney or penile tissue of the patient via the energy delivery element,
wherein at least partially ablating the neural fibers innervating the kidney or penile tissue results in a therapeutically beneficial reduction in one or more physiological conditions associated with erectile dysfunction of the patient.

30. The method of example 29, further comprising administering one or more pharmaceutical drugs to the patient, wherein the pharmaceutical drugs are selected from the group consisting of antihypertensive drugs, phosphodiesterase type 5 inhibitors and anti-diabetic drugs.

31. The method of example 29 or example 30 wherein the reduction in one or more physiological conditions associated with erectile dysfunction includes a reduction in the number of instances of impotence during sexual performance in the patient.

XII. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. For example, in additional embodiments, the system 100 may include a treatment device configured to deliver therapeutic energy to the patient from an external location outside the patient's body, i.e., without direct or close contact to the target site. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:
1. A method, comprising:
introducing a neuromodulation assembly at a distal portion of a treatment device proximate to a dorsal nerve of a penis of a human patient diagnosed with erectile dysfunction or low libido, wherein introducing the neuromodulation assembly comprises extracorporeally positioning the neuromodulation assembly on penile tissue;
partially disrupting function of the dorsal nerve by applying thermal energy to the dorsal nerve via the neuromodulation assembly, wherein thermal energy is applied via the neuromodulation assembly through penile skin; and
removing the neuromodulation assembly from the patient after treatment,
wherein partial disruption of the function of the dorsal nerve therapeutically treats the diagnosed erectile dysfunction or low libido.

2. The method of claim 1 wherein the patient is diagnosed with low libido, and wherein partial disruption of the function of the dorsal nerve reverses low libido in the patient.

3. The method of claim 1 wherein partially disrupting function of the dorsal nerve by applying thermal energy comprises at least partially ablating the dorsal nerve via thermal energy from the neuromodulation assembly.

4. The method of claim 1 wherein partially disrupting function of the dorsal nerve in a manner that therapeutically treats the diagnosed erectile dysfunction or low libido comprises increasing a frequency of penile erections in the patient.

5. The method of claim 4 wherein increasing a frequency of penile erections in the patient is self-reported by the patient within about three months to about 12 months after reducing sympathetic neural activity in the patient.

6. The method of claim 4 wherein increasing a frequency of penile erections is assessed using a nocturnal penile tumescence test.

7. The method of claim 1 wherein partially disrupting function of the dorsal nerve in a manner that therapeutically treats the diagnosed erectile dysfunction or low libido comprises reducing a number of incidences where the patient reports impotence or premature loss of erection by at least about 20%.

8. The method of claim 1 wherein partially disrupting function of the dorsal nerve in a manner that therapeutically treats the diagnosed erectile dysfunction or low libido comprises reducing an average patient-perceived or clinician-observed frequency of impotence or premature detumescence during sexual activity within about three months to about 12 months after reducing sympathetic neural activity in the patient.

9. The method of claim 1 wherein partially disrupting function of the dorsal nerve by applying thermal energy to the dorsal nerve via the neuromodulation assembly comprises applying ultrasound energy via the neuromodulation assembly.

* * * * *